US008029784B2

(12) United States Patent
Bates et al.

(10) Patent No.: US 8,029,784 B2
(45) Date of Patent: *Oct. 4, 2011

(54) METHOD FOR THE DIAGNOSIS AND PROGNOSIS OF MALIGNANT DISEASES

(75) Inventors: Paula J. Bates, Louisville, KY (US); Donald M. Miller, Louisville, KY (US); John O. Trent, Louisville, KY (US); Xiaohua Xu, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 170 days.

This patent is subject to a terminal disclaimer.

(21) Appl. No.: 12/041,969

(22) Filed: Mar. 4, 2008

(65) Prior Publication Data

US 2009/0017009 A1    Jan. 15, 2009

Related U.S. Application Data

(63) Continuation of application No. 10/683,480, filed on Oct. 9, 2003, now Pat. No. 7,357,928, which is a continuation-in-part of application No. 10/118,854, filed on Apr. 8, 2002, now Pat. No. 7,541,150.

(51) Int. Cl.
A61K 39/395 (2006.01)
(52) U.S. Cl. .................................... 424/130.1; 424/1.11
(58) Field of Classification Search .................. None
See application file for complete search history.

(56) References Cited

U.S. PATENT DOCUMENTS

| | | |
|---|---|---|
| 4,474,892 A | 10/1984 | Murad et al. |
| 4,522,811 A | 6/1985 | Eppstein et al. |
| 4,665,897 A | 5/1987 | Lemelson |
| 5,093,246 A | 3/1992 | Cech et al. |
| 5,192,660 A | 3/1993 | Reed-Gitomer |
| 5,545,807 A | 8/1996 | Surani et al. |
| 5,567,595 A | 10/1996 | Kok |
| 5,629,197 A | 5/1997 | Ring et al. |
| 5,736,348 A | 4/1998 | Goldenberg et al. |
| 5,770,429 A | 6/1998 | Lonberg et al. |
| 5,925,334 A | 7/1999 | Rubin et al. |
| 5,932,475 A | 8/1999 | Bandman et al. |
| 6,048,703 A | 4/2000 | Siman et al. |
| 6,096,532 A | 8/2000 | Armstrong et al. |
| 6,165,786 A | 12/2000 | Bennett et al. |
| 6,291,643 B1 | 9/2001 | Zou et al. |
| 6,306,404 B1 | 10/2001 | LaPosta et al. |
| 6,325,785 B1 | 12/2001 | Babkes et al. |
| 6,339,075 B1 | 1/2002 | King et al. |
| 6,350,452 B1 | 2/2002 | Riss |
| 6,462,189 B1 | 10/2002 | Koide |
| 6,506,559 B1 | 1/2003 | Fire et al. |
| 7,357,928 B2 | 4/2008 | Bates et al. |
| 2002/0028488 A1 | 3/2002 | Singh et al. |
| 2003/0194754 A1 | 10/2003 | Miller et al. |
| 2004/0132049 A1 | 7/2004 | Bates et al. |
| 2005/0026860 A1 | 2/2005 | Lin et al. |
| 2005/0053607 A1 | 3/2005 | Bates et al. |
| 2005/0187176 A1 | 8/2005 | Bates et al. |
| 2006/0258605 A1 | 11/2006 | Luo et al. |
| 2009/0017009 A1 | 1/2009 | Bates et al. |
| 2009/0226914 A1 | 9/2009 | Bates et al. |
| 2011/0065121 A1 | 3/2011 | Bates et al. |

FOREIGN PATENT DOCUMENTS

| | | |
|---|---|---|
| AU | 762572 | 11/1999 |
| DE | 10037861 | 2/2002 |
| JP | 07 242566 A | 9/1995 |
| WO | WO 95/20401 | 8/1995 |
| WO | WO 97/22250 | 6/1997 |
| WO | WO 98/24893 | 6/1998 |
| WO | WO 98/40480 | 9/1998 |
| WO | WO 99/06588 | 2/1999 |
| WO | WO 99/53057 | 10/1999 |
| WO | WO 00/61597 | 10/2000 |
| WO | WO 00/63250 | 10/2000 |
| WO | WO 01/32832 | 5/2001 |
| WO | WO 01/35093 | 5/2001 |
| WO | WO 01/68836 | 9/2001 |
| WO | WO 01/75164 | 10/2001 |
| WO | WO 01/91787 | 12/2001 |
| WO | WO 02/12437 | 2/2002 |
| WO | WO 02/44321 | 6/2002 |
| WO | WO 03/029277 | 4/2003 |
| WO | WO 03/008617 | 10/2003 |
| WO | WO 03/086174 | 10/2003 |
| WO | WO 03/087124 | 10/2003 |
| WO | WO 2004/003554 | 1/2004 |
| WO | WO 2005/035579 | 4/2005 |
| WO | WO 2009/088837 | 7/2009 |

OTHER PUBLICATIONS

Rubanyi (Molecular Aspects of Medecine 2001 ;22:113-142).*
Inder Verma (Nature Sep. 1997;389:239-242).*
Theodore Friedmann (Scientific American Jun. 1997, p. 96-101.*
Orkin and Motulsky NIH ad hoc committee Dec. 1995 http://www.nih.gov/news/pane/rep.html, p. 1.*
Gura (Science, v278, 1997, pp. 1041-1042).*
Abaza, M.S.I, et al, "Effects of amino acid substitutions outside an antigenic site on protein binding to monoclonal antibodies of predetermined specificity obtained by peptide immunization: Demonstration with region 94-100 (antigenic site 3) of myoglobin", Journal of Protein Chemistry, vol. 11, No. 5, pp. 433-444, (1992).
Agrawal, S, et al, "Antisense therapeutics: is it as simple as complementary base recognition?", Mol Med Today, vol. 6, No. 2, pp. 72-81, (2000).
Aihara, M, et al, "The frequency of apoptosis correlates with the prognosis of Gleason Grade 3 adenocarcinoma of the prostate", Cancer, vol. 75, No. 2, pp. 522-529, (1995).
Aihara, M, et al, "Frequency of apoptotic bodies positively correlates With Gleason grade in prostate cancer", Hum Pathol, vol. 25, No. 8, pp. 797-801, (1994).
Ali, S, et al, "Absorption, distribution, metabolism, and excretion of a respirable antisense oligonucleotide for asthma", Am J Respir Crit Care Med, vol. 163, No. 4, pp. 989-993, (2001).

(Continued)

Primary Examiner — Misook Yu
Assistant Examiner — Mark Halvorson
(74) Attorney, Agent, or Firm — Evan Law Group LLC

(57) ABSTRACT

Methods for the treatment of tumors and cancer by exploiting the surface expression of the usually nuclear-localized protein, nucleolin.

7 Claims, 4 Drawing Sheets

OTHER PUBLICATIONS

Altman, S, "Nobel lecture. Enzymatic cleavage of RNA by RNA", Biosci Rep, vol. 10, No. 4, pp. 317-337, (1990).

Alvarex-Gonzalez, R, et al, "Selective loss of poly(ADP-ribose) and the 85-kDa fragment of ply(ADP-ribose) polymerase in nucleoli during alkylation-induced apoptosis of HeLa Cells", J Biol Chem., vol. 274, No. 45, pp. 32122-32126, (1999).

Anderson, H.J, et al, "Flow cytometry of mitotic cells", Exp Cell Research, vol. 238, No. 2, pp. 498-502, (1998).

Andrade, F, et al, "Apoptosis in systemtic lupus erythematosus", Rheumatic Diseases Clinics of North America, vol. 2, (2000).

Awang, G, et al, "Mode of dimerization of HIV-1 genomic RNA", Biochemistry, vol. 32, No. 42, pp. 11453-11457, (1993).

Ballou, B, et al, "Three-Dimensional Imaging of Nucleolin Trafficking in Normal Cells, Transfectants, and Heterokaryons", SPIE, vol. 2680, pp. 124-131, (1996).

Ballou, B, et al, "Tumor Detection and Visualization Using Cyanine Fluorochrome-Labeled Antibodies", Biotechnol Prog, vol. 13, pp. 649-658, (1997).

Ballou, B, et al, "Tumor Labeling in Vivo Using Cyanine-Conjugated Monoclonal Antibodies", Cancer Immunol Immunother, vol. 41, pp. 257-263, (1995).

Ballou, B, et al, Abstract of "Cyanine Fluorocrome-Labeled Antibodies in Vivo: Assessment of Tumor Imaging Using Cy3, Cy5, Cy5.5, and Cy7", Cancer Detect Prey, vol. 22, No. 3, pp. 251-257, (1998).

Baran, N, et al, "The SV40 large T-antigen helicase can unwind four stranded DNA structures linked by G-quartets", Nucleic Acids Research, vol. 25, No. 2, pp. 297-303, (1997).

Barton, C.M, et al, "Antisense oligonucleotides directed against p53 have antiproliferative effects unrelated to effects on p53 expression", Br J Cancer, vol. 71, No. 3, pp. 429-437, (1995).

Bates, P.J, et al, "Antiproliferative activity of G-rich oligonucleotides correlates with protein binding", The Journal of Biological Chemistry, vol. 274, No. 37, pp. 26369-26377, (1999).

Beedassy, A, et al, "Chemotherapy in advanced prostate cancer", Semin Oncol, vol. 26, No. 4, pp. 428-438, (1999).

Beltinger, C, et al, "Binding, uptake, and intracellular trafficking of phosphorothioate-modified oligodeoxynucleotides", J Clin Invest, vol. 95, No. 4, pp. 1814-1823, (1995).

Benimetskaya, L, et al, "Formation of a G-tetrad and higher order structures correlates with biological activity of the RelA (NF-kappaB p65) 'antisense' oligodeoxynucleotide", Nucleic Acids Research, vol. 25, No. 13, pp. 2648-2656, (1997).

Benton, B.M, et al, "A novel FK506- and rapamycin-binding protein (FPR3 gene product) in the yeast Saccharomyces cerevisiae is a praline rotamase localized to the nucleolus", J Cell Biol, vol. 127, No. 3, pp. 623-639, (1994).

Bergsmedh, A, et al, "Horizontal transfer of oncogenes by uptake of apoptotic bodies", Proc Natl Acad Science USA, vol. 98, No. 11, pp. 6407-6411, (2001).

Bergsmedh, A, et al, "Loss of the p21(Cip1/Waf1) cyclin kinase inhibitor results in propagation of horizontally transferred DNA", Cancer Research, vol. 62, No. 2, pp. 575-579, (2002).

Bernardi, F.D, et al, "A prognostic model of survival in surgically resected squamous cell carcinoma of the lung using clinical, pathologic, and biologic markers", Mod Pathol, vol. 10, No. 10, pp. 992-1000, (1997).

Bernstein, E, et al, "Role for a bidentate ribonuclease in the initiation step of RNA interference", Nature, vol. 409, No. 6818, pp. 363-366, (2001).

Bharti, A.K, et al, "Identification of a nucleolin binding site in human topoisomerase I", J Biol Chem, vol. 271, No. 4, pp. 1993-1997, (1996).

Biggiogera, M, et al, "Heterogeneous ectopic RNP-derived structures (HERDS) are markers of transcriptional arrest", FASEB J, vol. 14, No. 5, pp. 828-834, (2000).

Biscotti, C.V, et al, "Apoptotic bodies: a consistent morphologic feature of endocervical adenocarcinoma in situ", American Journal of Surgical Pathology, vol. 22, No. 4, pp. 434-439, (1998).

Bishop, J.S, et al, "Intramolecular G-quartet motifs confer nuclease resistance to a potent anti-HIV oligonucleotide", J Biol Chem, vol. 271, No. 10, pp. 5698-5703, (1996).

Blau, H.M, et al, "Tet B or not tet B: Advances in tetracycline-inducible gene expression", Proc Natl Acad Science USA, vol. 96, pp. 797-799, (1999).

Bock, L.C, et al, "Selection of single-stranded DNA molecules that bind and inhibit human thrombin", Nature, vol. 355, No. 6360, pp. 564-566, (1992).

Borer, R.A, et al, "Major nucleolar proteins shuttle between nucleus and cytoplasm", Cell, vol. 56, No. 3, pp. 379-390, (1989).

Borggrefe, T, et al, "A B-cell-specific DNA recombination complex", J Biol Chem, vol. 273, No. 27, pp. 17025-17035, (1998).

Borst, P, et al, "Does resistance to apoptosis affect clinical response to antitumor drugs?", Drug Resist Update, vol. 4, No. 2, pp. 129-131, (2001).

Bortul, R, et al, "Nuclear changes in necrotic HL-60 cells", J Cell Biochem, vol. 81, No. S36, pp. 19-31, (2001).

Boulares, A.H, et al, "Role of poly (ADP-ribose) polymerase (PARP) cleavage in apoptosis. Caspase 3-resistant PARP mutant increases rates of apoptosis in transfected cells", Journal of Biological Chemistry, vol. 274, No. 33, pp. 22932-22940, (1999).

Boulares, A.H, et al, "Roles of DNA fragmentation factor and poly(ADP-ribose) polymerase in an amplification phase of tumor necrosis factor-induced apoptosis", Journal of Biological Chemistry, vol. 276, No. 41, pp. 38185-38192, (2001).

Brockstedt, E, et al, "Identification of apoptosis-associated proteins in a human Burkitt lymphoma cell line. Cleavage of heterogeneous nuclear ribonucleoprotein A1 by caspase 3", J Biol Chem, vol. 273, No. 43, pp. 28057-28064, (1998).

Brown, J.M, et al, "Apoptosis:mediator or mode of cell killing by anticancer agents?", Drug Resist Update, vol. 4, No. 2, pp. 135-136, (2001).

Brustmann, H, "Apoptotic bodies as a morphological feature in serous ovarian carcinoma: correlation with nuclear grade, Ki-67 and mitotic indices", Pathol Res Pract, vol. 198, No. 2, pp. 85-90, (2002).

Burgess, T.L, et al, "The antiproliferative activity of c-myb and c-myc antisense oligonucleotides in smooth muscle cells is caused by a nonantisense mechanism", Proc Natl Acad Science USA, vol. 92, No. 9, pp. 4051-4055, (1995).

Buys, C.H, "Telomeres, telomerase, and cancer", N Engl J Med, vol. 342, No. 17, pp. 1282-1283, (2000).

Callebaut, C, et al, "Identification of V3 loop-binding proteins as potential receptors implicated in the binding of HIV particles to CD4(+) cells", J Biol Chem, vol. 273, No. 34, pp. 21988-21997, (1998).

Cannavo, G, et al, "Abnormal intracellular kinetics of cell-cycle-dependent proteins in lymphocytes from patients infected with human immunodeficiency virus: a novel biologic link between immune activation, accelerated t-cell turnover, and high levels of apoptosis", Blood, vol. 97, No. 6, pp. 1756-1764, (2001).

Carney, D.N, et al, "Establishment and identification of small cell lung cancer cell lines having classic and variant features", Cancer Research, vol. 45, pp. 2913-2923, (1985).

Carvalho, P.E, et al, "Useful prognostic panel markers to express the biological tumor status in resected lung adenocarcinomas", Jpn J Clin Oncol, vol. 30, No. 11, pp. 478-486, (2000).

Cech, T.R, "Biologic catalysis by RNA", Harvey Lect, vol. 82, pp. 123-144, (1988).

Chern, J.H, et al, "Usefulness of AgNOR score in differentiating benign from malignant pulmonary aspiration cytology", Acta Cytol, vol. 41, No. 2, pp. 393-398, (1997).

Choi, N. G, et al, "Apoptosis and nuclear shapes in benign prostate hyperplasia and prostate adenocarcinoma: comparison with and relation to Gleason score", Int J Urol, vol. 6, No. 1, pp. 13-18, (1999).

Cole, S.P, et al, "Antibody production by human X human hybridomas in serum-free medium", J Immunol Methods, vol. 78, No. 2, pp. 271-278, (1985).

Coligan, J.E. et al., "Production of Monoclonal Antibodies", Current Protocols in Immunology, vol. 1, pp. 2.5.1-2.6.7, Wiley, New York, (1991).

Coqueret, O, et al, "Functional interaction of STAT3 transcription factor with the cell cycle inhibitor p21$^{WAF1/CIP1/SDI1}$", J Biol Chem, vol. 275, No. 25, pp. 18794-18800, (2000).

Cowan, K.H, et al, "Dihydrofolate reductase gene amplification and possible rearrangement in estrogen-responsive methotrexate-resistant human breast cancer cells", J Biol Chem, vol. 257, No. 24, pp. 15079-15086, (1982).

Crooke, S., "Oligonucleotide therapeutics: a prospectus." Antisense Research and Development, vol. 3, No. 1, pp. 1-2, (1993).

Crooke, S, "Progress in antisense technology: the end of the beginning", Methods Enzymol, vol. 313, pp. 3-45, (1999).

D'Amours, D, et al, "Poly(ADP-ribosyl)ation reactions in the regulation of nuclear functions", Biochem J, vol. 342, pt. 2, pp. 249-268, (1999).

Dagle, J.M, et al, "Selective degradation of targeted mRNAs using partially modified oligonucleotides", Methods Enzymol, vol. 313, pp. 420-436, (1999).

Daniely, Y, et al, "Formation of a complex between nucleolin and replication protein A after cell stress prevents initiation of DNA replication", J Cell Biology, vol. 149, No. 4, pp. 799-810, (2000).

Dapic, V, et al, "Antiproliferative activity of G-Quartet-forming oligonucleotides with backbone and sugar modifications", Biochemistry, vol. 41, No. 11, pp. 3676-3685, (2002).

David, K, et al, "Initial characterization of the apoptosis-inducing receptor for natural human anti-neuroblastoma IgM", Med Pediatr Oncol, vol. 36, No. 1, pp. 251-257, (2001).

David-Pfeuty, T, "Potent inhibitors of cyclin-dependent kinase 2 induce nuclear accumulation of wild-type p53 and nucleolar fragmentation in human untransformed and tumor-derived cells", Oncogene, vol. 18, No. 52, pp. 7409-7422, (1999).

Davis, K.A, et al, "Staining of cell surface human CD4 with 2'-F-pyrimidine-containing RNA aptamers for flow cytometry", Nucleic Acids Research, vol. 26, pp. 3915-3924, (1998).

De Jong, J.S, et al, "Number of apoptotic cells as a prognostic marker in invasive breast cancer", Br J Cancer, vol. 82, No. 2, pp. 368-373, (2000).

Dempsey, L.A, et al, "A specific isoform of hnRNP D interacts with DNA in the LR1 heterodimer: canonical RNA binding motifs in a sequence-specific duplex DNA binding protein", J Biol Chem, vol. 273, No. 44, pp. 29224-29229, (1998).

Dempsey, L.A, et al, "G4 Dna binding by LR1 and its subunits, nucleolin and hnRNP D, A role for G-G pairing in immunoglobulin switch recombination", J Biol Chem, vol. 274, No. 2, pp. 1066-1071, (1999).

Deng, J.S, et al, "Internalization of anti-nucleolin antibody into viable HEp-2 cells", Mol Biol Rep, vol. 23, No. 3-4, pp. 191-195, (1996).

Derenzini, M. "The AgNORs", Micron, vol. 31, No. 2, pp. 117-120, (2000).

Derenzini, M, et al, "The quantity of nucleolar proteins nucleolin and protein B23 is related to cell doubling time in human cancer cells", Lab Invest, vol. 73, No. 4, pp. 497-502, (1995).

Desnoyers, S, et al, "Alteration of the nucleolar localization of poly(ADP-ribose) polymerase upon treatment with transcription inhibitors", Exp Cell Research, vol. 227, No. 1, pp. 146-153, (1996).

Dickinson, L.A, et al, "Nucleolin is a matrix attachment region DNA-binding protein that specifically recognizes a region with high base-unpairing potential", Mol Cell Biology, vol. 15, No. 1, pp. 456-465, (1995).

Dranovsky, A, et al, "Cdc2 phosphorylation of nucleolin demarcates mitotic stages and alzheimer's disease pathology", Neurobiol Aging, vol. 22, No. 4, pp. 517-528, (2001).

Drews, J, "Drug discovery: a historical perspective", Science, vol. 287, No. 5460, pp. 1960-1964, (2000).

Drews J, et al, "Classic drug targets (special pull-out)", Nature Biotechnology, vol. 15, (1997).

Dryden, S, et al, "The lack of specificity of neuropeptide Y (NPY) antisense oligodeoxynucleotides administered intracerebroventricularly in inhibiting food intake and NPY gene expression in the rat hypothalamus", J Endocrinol, vol. 157, No. 1, pp. 169-175, (1998).

Dumler, I, et al, "Urokinase-induced mitogenesis is mediated by casein kinase 2 and nucleolin", Curr Biol, vol. 9, No. 24, pp. 1468-1476, (1999).

Dundr, M, et al, "The dynamics of postmitotic reassembly of the nucleolus", J Cell Biol, vol. 150, No. 3, pp. 433-446, (2000).

Edwards, T.K, et al, "Role for nucleolin/Nsr1 in the cellular localization of topoisomerase I", J Biol Chem, vol. 275, No. 46, pp. 36181-36188, (2000).

Eguchi, K, "Apoptosis in autoimmune diseases", Intern Med, vol. 40, No. 4, pp. 275-284, (2001).

Erard, M.S, et al, "A major nucleolar protein, nucleolin, induces chromatin decondensation by binding to histone H1", Eur J Biochem, vol. 175, No. 3, pp. 525-530, (1988).

European Search Report for Application No. 03728350.4 dated Jul. 12, 2005.

Facompre, M, et al, "Apoptotic response of HL-60 human leukemia cells to the antitumor drug NB-506, a glycosylated indolocarbazole inhibitor of topoisomerase 1", Biochem Pharmacol, vol. 61, No. 3, pp. 299-310, (2001).

Feltzer, R.E, et al, "Alkaline proteinase inhibitor of *Pseudomonas aeruginosa*. Interaction of native and N-terminally truncated inhibitor proteins with Pseudomonas metalloproteinases", J Biol Chem, vol. 275, No. 28, pp. 21002-21009, (2000).

Fielding, P, et al, "Heterogeneous nuclear ribonucleoprotein A2/B1 up-regulation in bronchial lavage specimens: a clinical marker of early lung cancer detection", Clincal Cancer Research, vol. 5, No. 12, pp. 4048-4052, (1999).

Fry, M, et al, "Human Werner syndrome DNA helicase unwinds tetrahelical structures of the fragile X syndrome repeat sequence d(CGG)n", J Biol Chem, vol. 274, No. 18, pp. 12797-12802, (1999).

Fry, M, et al, "The fragile X syndrome d(Cgg)n. nucleotide repeats form a stable tetrahelical structure", Proc Natl Acad Science USA, vol. 91, No. 11, pp. 4950-4954, (1994).

Gascoyne, R.D, et al, "Prognostic significance of Bcl-2 protein expression and Bcl-2 gene rearrangement in diffuse aggressive non-Hodgkin's lymphoma", Blood, vol. 90, No. 1, pp. 244-251, (1997).

Gautier, F, et al, "Identification of an apoptotic cleavage product of BARD1 as an autoantigen: a potential factor in the antitumoral response mediated by apoptotic bodies", Cancer Research, vol. 60, No. 24, pp. 6895-6900, (2000).

Gautier, F, et al, "Production and characterisation of a monoclonal antibody specific for apoptotic bodies derived from several tumour cell lines", Journal of Immunological Methods, vol. 228, pp. 49-58, (1999).

Gavrieli, Y, et al, "Identification of programmed cell death in situ via specific labeling of nuclear DNA fragmentation", the Journal of Cell Biology, vol. 119, No. 3, pp. 493-501, (1992).

Gey, G, et al, "Tissue culture studies of the proliferative capacity of cervical carcinoma and normal epithelium", Cancer Research, vol. 12, pp. 264, (1952).

Ghosh, M, et al, "Apoptosis in squamous cell carcinoma of the lung: correlation with survival and clinicopathological features", J Clin Pathol, vol. 54, No. 2, pp. 111-115, (2001).

Giaccone, G, et al, "Neuromedin B is present in lung cancer cell lines", Cancer Research, vol. 52, pp. 2732s-2736s, (1992).

Gibbs, J.B, "Mechanism-based target identification and drug discovery in cancer research", Science, vol. 287, No. 5460, pp. 1969-1973, (2000).

Gil, D, et al, "Intracellular redistribution of nucleolin upon interaction with the CD3epsilon chain of the T cell receptor complex", J Biol Chem, vol. 276, No. 14, pp. 11174-11179, (2001).

Giles, R.V, et al, "Selecting optimal oligonucleotide composition for maximal antisense effect following streptolysin O—mediated delivery into human leukaemia cells", Nucleic Acids Research, vol. 26, No. 7, pp. 1567-1575, (1998).

Gilloteaux, J. et al., "Cancer cell necrosis by autoschizis: synergism of antitumor activity of vitamin C: vitamin $K_3$ on human bladder carcinoma T24 cells", Scanning, vol. 20, No. 8, pp. 564-575, (1998).

Ginisty, H, et al, "Structure and functions of nucleolin", J Cell Science, vol. 112, Pt. 6, pp. 761-772, (1999).

Giovannangeli, C. et al, "Progress in developments of triplex-based strategies", Antisense & Nucleic Acid Drug Development, vol. 7, No. 4, pp. 413-421, (1997).

Giraldo, R, et al, "The yeast telomere-binding protein RAP1 binds to and promotes the formation of DNA quadruplexes in telomeric DNA", EMBO J, vol. 13, No. 10, pp. 2411-2420, (1994).

Green, D. W, et al, "Beta-catenin antisense treatment decreases beta-catenin expression and tumor growth rate in colon carcinoma xenografts", J Surg Res, vol. 101, No. 1, pp. 16-20, (2001).

Grinstein, E, et al, "Nucleolin as Activator of Human Papillomavirus Type 18 Oncogene Transcription in Cervical Cancer", J Exp Med, vol. 196, No. 8, pp. 1067-1078, The Rockefeller University Press, (2002).

Gudas, J.M, et al, "Drug-resistant breast cancer cells frequently retain expression of a functional wild-type p53 protein", Carcinogenesis, vol. 17, No. 7, pp. 1417-1427, (1996).

Haese, A, "Serum markers for early detection and staging of prostate cancer, status report on current and future markers", Urologe A, vol. 42, No. 9, pp. 1172-1187, (2003).—(Abstract Only).

Halicka, H.D, et al, "Segregation of RNA and separate packaging of DNA and RNA in apoptotic bodies during apoptosis", Exp Cell Research, vol. 260, No. 2, pp. 248-256, (2000).

Hanahan, D, et al, "The hallmarks of cancer", Cell, vol. 100, No. 1, pp. 57-70, (2000).

Hanakahi, L.A, et al, "High affinity interactions of nucleolin with G-G-paired rDNA", J Biol Chem, vol. 274, No. 22, pp. 15908-15912, (1999).

Hanakahi, L.A, et al, "Nucleolin is one component of the B cell-specific transcription factor and switch region binding protein, LR1", Proc Natl Acad Science USA, vol. 94, No. 8, pp. 3605-3610, (1997).

Harms, G, et al, "Identification of nucleolin as a new L-selectin ligand", Biochem J, vol. 360, pp. 531-538, (2001).

Herceg, Z, et al, "Failure of poly(ADP-ribose) polymerase cleavage by caspases leads to induction of necrosis and enhanced apoptosis", Mol Cell Biol, vol. 19, No. 7, pp. 5124-5133, (1999).

Hirata, D, et al, "Nucleolin as the earliest target molecule of autoantibodies produced in MRL1/lpr lupus-prone mice", Clin Immunol, vol. 97, No. 1, pp. 50-58, (2000).

Hirsch, F.R, et al, "Early detection of lung cancer: clinical perspectives of recent advances in biology and radiology", Clinical Cancer Research, vol. 7, No. 1, pp. 5-22, (2001).

Holdenrieder, S, et al, "Nucleosomes in serum as a marker for cell death", Clin Chem Lab Med, vol. 39, No. 7, pp. 596-605, (2001).

Holdenrieder, S, et al, "Nucleosomes in serum of patients with benign and malignant diseases", Int. J. Cancer, vol. 95, pp. 114-120, (2001).

Holdenrieder, S, et al, "Circulating nucleosomes in serum", Annals New York Academy of Sciences, vol. 945, pp. 93-102, (2001).

Holdenrieder, S, et al, "Quantification of nucleosomes in serum by the cell death detection ELISAplus", Biochemica, No. 1, pp. 25-27, (2002), (http://www.roche-applied-science.com/biochemica/no1_02/PDF/p25.pdf).

Holmgren, L, et al, "Horizontal transfer of DNA by the uptake of apoptotic bodies", Blood, vol. 93, No. 11, pp. 3956-3963, (1999).

Horky, M, et al, "Segregation of nucleolar components coincides with caspase-3 activation in cisplatin-treated HeLa cells", J Cell Science, vol. 114, pt. 4, pp. 663-670, (2001).

Hovanessian, A.G, et al, "The cell-surface-expressed nucleolin is associated with the actin cytoskeleton", Experimental Cell Research, vol. 261, pp. 312-328, (2000).

Huang, Z, "Bcl-2 family proteins as targets for anticancer drug design", Oncogene, vol. 19, No. 56, pp. 6627-6631, (2000).

Iida, A, et al, "Inducible gene expression by retrovirus-mediated transfer of a modified tetracycline-regulated system", J Virol, vol. 70, No. 9, pp. 6054-6059, (1996).

International Search Report dated Nov. 13, 2003 for PCT application No. PCT/US03/20167.

International Search Report dated Aug. 3, 2004 for PCT application No. PCT/US03/10745.

International Search Report dated Mar. 14, 2005 for PCT application No. PCT/USO4/033174.

Irving, R.A, et al, "Ribosome display and affinity maturation: from antibodies to single v-domains and steps towards cancer therapeutics", J Immunol Methods, vol. 248, issues 1-2, pp. 31-45, (2001).

Ishikawa, F, et al, "Nuclear proteins that bind the pre-mRNA 3' splice site sequence r(UUAG/G) and the human telomeric DNA sequence d(TTAGGG)n", Mol Cell Biology, vol. 13, No. 7, pp. 4301-4310, (1993).

Jordan, P, et al, "Major cell surface-located protein substrates of an ecto-protein kinase are homologs of known nuclear proteins", Biochemistry, vol. 33, No. 49, pp. 14696-14706, (1994).

Jungblut, P.R, et al, "Proteomics in human disease: cancer, heart and infectious diseases", Electrophoresis, vol. 20, No. 10, pp. 2100-2110, (1999).

Kamma, H, et al, "Interaction of hnRNP A2/B1 isoforms with telomeric ssDNA and the in vitro function", Biochem Biophys Res Commun, vol. 280, No. 3, pp. 625-630, (2001).

Kaneko, S, et al, "Nucleolar organizer regions as a prognostic indicator for stage I non-small cell lung cancer", Cancer Research, vol. 51, No. 15, pp. 4008-4011, (1991).

Kennedy, T.C, et al, "Screening for lung cancer revisited and the role of sputum cytology and fluorescence bronchoscopy in a high-risk group", Chest, vol. 117, supplemental 4, pp. 72S-79S, (2000).

Keough, T, et al, "A method for high-sensitivity peptide sequencing using postsource decay matrix-assisted laser desorption ionization mass spectrometry", Proc Nati Acad Science USA, vol. 96, No. 13, pp. 7131-7136, (1999).

Kerr, J.F, et al, "Apoptosis: a basic biological phenomenon with wide-ranging implications in tissue kinetics", Br J Cancer, vol. 26, pp. 239-257, (1972).

Ketting, R.F, et al, "Dicer functions in RNA interference and in synthesis of small RNA involved in developmental timing in C elegans", Genes Dev, vol. 15, No. 20, pp. 2654-2659, (2001).

Kibbey, M.C, et al, "A 110-kD nuclear shuttling protein, nucleolin, binds to the neurite-promoting IKVAV site of laminin-1", J Neurosci Research, vol. 42, No. 3, pp. 314-322, (1995).

Kim, C.S, et al, "A micro double capillary method for rheologic measurements of lower airway secretions", Bull Eur Physiopathol Respir, vol. 18, pp. 915-927, (1982).

Knorre, D.G. et al., "Antisense oligonucleotide derivatives as gene-targeted drugs", Biomed Sci, vol. 1, No. 4, pp. 334-343, (1990).

Kohler, G, et al, "Continuous cultures of fused cells secreting antibody of predefined specificity", Nature, vol. 256, pp. 495-497, (1975).

Kohler, P.O, "Isolation, cloning, and hybridization of endocrine cell lines", Methods Enzymol, vol. 39, pp. 109-128, (1975).

Krantz, S, et al, "Purification and partial amino acid sequencing of a fructosyllysine-specific binding protein from cell membranes of the monocyte-like cell line U937", Biochim Biophys Acta, vol. 1266, No. 1, pp. 109-112, (1995).

Kuby, J, "Antigens", Immunology, Second Edition, chapter 4, pp. 85-96, W.H. Freeman and Company, New York, (1994).

Kumar, R.K, et al, "Improved double immunofluorescence for confocal laser scanning microscopy", J Histochem Cytochem, vol. 47, No. 9, pp. 1213-1218, (1999).

Kwiatkowski, B.A, et al, "Identification and cloning of a novel chromatin-associated protein partner of Epstein-Barr nuclear protein 2", Experimental Cell Research, vol. 300, pp. 223-233, (2004).

Lakka, S.S, et al, "Adenovirus-mediated antisense urokinase-type plasminogen activator receptor gene transfer reduces tumor cell invasion and metastasis in non-small cell lung cancer cell lines", Clinical Cancer Research, vol. 7, No. 4, pp. 1087-1093, (2001).

Langer, P.R, et al, "Enzymatic synthesis of biotin-labeled polynucleotides: novel nucleic acid affinity probes", Proc Natl Acad Sci USA, vol. 78, pp. 6633-6637, (1981).

Larrucea, S. et. al, "Internalization of factor J and and cellular signalization after factor J-cell interaction", Biochem Biophys Res Commun, vol. 266, No. 1, pp. 51-57, (1999).

Larrucea, S, et al, "Cellular adhesion mediated by factor J, a complement inhibitor. Evidence for nucleolin involvement", J Biol Chem, vol. 273, No. 48, pp. 31718-31725, (1998).

Lau, Q.C, et al, "In vivo pro-apoptotic and antitumor efficacy of a c-Raf antisense phosphorothioate oligonucleotide: relationship to tumor size", Antisense Nucleic Acid Drug Development, vol. 12, No. 1, pp. 11-20, (2002).

Lebedeva, I, et al, "Antisense oligonucleotides: promise and reality", Annu Rev Pharmacol Toxicol, vol. 41, pp. 403-419, (2001).

Leitinger, N, et al, "ADP-ribosylation of nucleolar proteins in HeLa tumor cells", J Cell Biochem, vol. 52, No. 2, pp. 153-158, (1993).

Lichtenstein, A.V, et al, "Circulating nucleic acids and apoptosis", Annuals New York Academy of Sciences, vol. 945, pp. 239-249, (2001).

Lin, D.L, et al, "p53 is a mediator for radiation-repressed human TR2 orphan receptor expression in MCF-7 cells, a new pathway from tumor suppressor to member of the steroid receptor superfamily", J Biol Chem, vol. 271, pp. 14649-14652, (1996).

Lin, S, et al, "The biochemical status of the DNA synthesome can distinguish between permanent and temporary cell growth arrest", Cell Growth Differ, vol. 8, No. 12, pp. 1359-1369, (1997).

Little, C.D, et al, "Amplification and expression of the c-myc oncogene in human lung cancer cell lines", Nature, vol. 306, pp. 194-196, (1983).

Liu, H, et al, "Construction of a GAL1-regulated yeast cDNA expression library and its application to the identification of genes whose overexpression causes lethality in yeast", Genetics, vol. 132, No. 3, pp. 665-673, (1992).

Lopes de Menezes, D, et al, "Pharmacokinetics of Bcl-2 antisense oligonucleotide (G3139) combined with doxorubicin in SCID mice bearing human breast cancer solid tumor xenografts", Cancer Chemother Pharmacol, vol. 49, No. 1, pp. 57-68, (2002).

Lovborg, H, et al, "Modulation of pyridyl cyanoguanidine (CHS 828) induced cytotoxicity by 3-aminobenzamide in U-937 GTB cells", Biochem Pharmacol, vol. 63, No. 8, pp. 1491-1498, (2002).

Ma J, et al, "Cells designed to deliver anticancer drugs by apoptosis", Cancer Research, vol. 62, No. 5, pp. 1382-1387, (2002).

Mann, M, et al, "Analysis of proteins and proteomes by mass spectrometry", Annu Rev Biochem, vol. 70, pp. 437-473, (2001).

Martelli, A.M, et al, "Biochemical and Morphological characterization of the nuclear matrix from apoptotic HL-60 Cells", Journal of Cellular Biochemistry, vol. 72, No. 1, pp. 35-46, (1999).

Martelli, A.M, et al, "Behavior of nucleolar proteins during the course of apoptosis in camptothecin-treated HL60 cells", Journal of Cellular Biochemistry, vol. 78, No. 2, pp. 264-277, (2000).

Martelli, A.M, et al, "Nuclear apoptotic changes: an overview", J Cell Biochem, vol. 82, No. 4, pp. 634-646, (2001).

Martin, S.J, et al, "Protease activation during apoptosis: death by a thousand cuts?" Cell, vol. 82, pp. 349-352, (1995).

Matthews, D.A, "Adenovirus protein V induces redistribution of nucleolin and B23 from nucleolus to cytoplasm", J Virol, vol. 75, No. 2, pp. 1031-1038, (2001).

Mattson, M.P., "Apoptosis in neurodegenerative disorders", Nature Reviews Mol Cell Biology, vol. 1, No. 2, pp. 120-129, (2000).

Mayer, T.U, et al, "Small molecule inhibitor of mitotic spindle bipolarity identified in a phenotype-based screen", Science, vol. 286, No. 5441, pp. 971-974, (1999).

McEwen, C.N, et al, "Negative gold ion gun for liquid secondary ion mass spectrometry", Anal Chem, vol. 57, No. 4, pp. 890-892, (1985).

McManus, M.T, et al, "Gene silencing in mammals by small interfering RNAs." Nat Rev Genet, vol. 3, No. 10, pp. 737-747, (2002).

McManus, M.T, et al, "Gene silencing using micro-RNA designed hairpins", RNA, vol. 8, No. 6, pp. 842-850, (2002).

McNicol, A.M, et al, "Optimizing immunohistochemistry: antigen retrieval and signal amplification", Histopathology, vol. 32, pp. 97-103, (1998).

Mehes, G, et al, "Nucleolin and fibrillarin expression in stimulated lymphocytes and differentiating HL-60 cells. A flow cytometric assay", Cell Prolif, vol. 28, No. 6, pp. 329-336, (1995).

Mi, Y, et al, "Validation of Nucleolin as a Novel Target for Cancer Drug Discovery", Proceedings of the American Association for Cancer Research Annual Meeting, vol. 43, Mar. 2002, pp. 959-960, 93rd Annual Meeting of the American Association for Cancer Research, San Francisco, California, USA, Apr. 6-10, 2002.

Mickey, D.D, et al, "Heterotransplantation of a human prostatic adenocarcinoma cell line in nude mice", Cancer Research, vol. 37, pp. 4049-4058, (1977).

Mikolajczyk, S, et al, "Tumor-associated forms of prostate specific antigen improve the discrimination of prostate cancer from benign disease", Rinsho Byori, vol. 52, No. 3, pp. 223-230, (2004).

Minota, S, et al, "Autoantibodies to nucleolin in systemic lupus erythematosus and other diseases", J Immunol, vol. 146, No. 7, pp. 2249-2252, (1991).

Miranda, G.A, et al, "The murine nucleolin protein is an inducible DNA and ATP binding protein which is readily detected in nuclear extracts of lipopolysaccharide-treated splenocytes", Exp Cell Research, vol. 217, No. 2, pp. 294-308, (1995).

Morgan, D.M, "Tetrazolium (MTT) assay for cellular viability and activity", Meth Mol Biol, vol. 79, pp. 179-183, (1998).

Morimoto, Y, et al, "Alteration of argyrophilic nucleolar organizer region associated (Ag-NOR) proteins in apoptosis-induced human salivary gland cells and human oral aquamous carcinoma cells", J Oral Pathol Med, vol. 30, No. 4, pp. 193-199, (2001).

Morimoto, Y, et al, "Upregulation of the expression of Fas antigen and Fas ligand in a Human submandibular gland ductal cell line by okadaic acid", Arch Oral Biol, vol. 45, No. 8, pp. 657-666, (2000).

Morrison, S.L. et al, "Chimeric human antibody molecules: mouse antigen-binding domains with human constant region domains", Proceedings of the National Academy of Science USA, vol. 81, No. 21, pp. 6851-6855, (1984).

Murchie, A.I, et al, "Retinoblastoma susceptibility genes contain 5' sequences with a high propensity to form guanine-tetrad structures", Nucleic Acids Research, vol. 20, No. 1, pp. 49-53, (1992).

Naito, M, et al, "ATP/$Mg^{2+}$ -dependent binding of vincristine to the plasma membrane of multifrugresistant K562 cells", J Biol Chem, vol. 263, pp. 11887-11891, (1988).

Nakanishi, K, et al, "Argyrophilic nucleolar-organizer region counts and DNA status in bronchioloalveolar epithelial hyperplasia and adenocarcinoma of the lung", Hum Pathol, vol. 29, No. 3, pp. 235-239, (1998).

Navenot, J.M, et al, "Molecular anatomy of CCR5 engagement by physiologic and viral chemokines and HIV-1 envelope glycoproteins: differences in primary structural requirements for RANTES, MIP-1 alpha, and vMIP-II Binding", J Mol Biol, vol. 313, No. 5, pp. 1181-1193, (2001).

Neuberger, M.S, et al, "Recombinant antibodies possessing novel effector functions", Nature, vol. 312, No. 5995, pp. 604-608, (1984).

Nichols, R.C, et al, "The RGG domain in hnRNP A2 affects subcellular localization", Exp Cell Research, vol. 256, No. 2, pp. 522-532, (2000).

Nonomura, A, et al, "Demonstration of nucleolar organizer regions in lung carcinoma by silver staining", Surgery Today, vol. 23, pp. 486-490, (1993).

Norgaard, J.M, et al, "Fab M4 and high CD14 surface expression is associated with high cellular resistance to Ara-C and daunorubicin: implications for clinical outcome in acute myeloid leukaemia", European Journal of Haematology, vol. 67, pp. 221-229, (2001).

Nosseri, C, et al, "Possible involvement of poly(ADP-ribosyl) polymerase in triggering stress-induced apoptosis", Exp Cell Research, vol. 212, No. 2, pp. 367-373, (1994).

Ohkoudo, M, et al, "Morphometrical analysis of nucleolin immunohistochemistry in meningiomas", Acta Neuropathol, vol. 92, pp. 1-7, (1996).

Orfao, A, et al, "General concepts about cell sorting techniques", Clin Biochem, vol. 29, pp. 5-9, (1996).

Oyama, T, et al, "Nucleolar organizer regions are independently associated with a shortened survival in patients with non-small cell lung cancer", Surg Oncol, vol. 2, No. 6, pp. 341-347, (1993).

Paddison, P.J, et al, "Short hairpin RNAs (shRNAs) induce sequence-specific silencing in mammalian cells", Genes Dev, vol. 16, No. 8, pp. 948-958, (2002).

Paddison, P.J, et al, "Stable suppression of gene expression by RNAi in mammalian cells", Proc Nati Acad Science USA, vol. 99, No. 3, pp. 1443-1448, (2002).

Palomba, L, et al, "Apoptosis and necrosis following exposure of U937 cells to increasing concentrations of hydrogen peroxide: the effect of the poly(ADP-ribose) polymerase inhibitor 3-aminobenzamide", Biochem Pharmacol, vol. 58, No. 11, pp. 1743-1750, (1999).

Pandey, A, et al, "Proteomics to study genes and genomes", Nature, vol. 405, No. 6788, pp. 837-846, (2000).

Partridge, M. et al., "A simple method for delivering morpholino antisense oligos into the cytoplasm of cells", Antisense Nucleic Acid Drug Development, vol. 6, No. 3, pp. 169-175, (1996).

Pasternack, M.S, et al, "Granzyme a binding to target cell proteins Granzyme a binds to and cleaves nucleolin in vitro", J Biol Chem, vol. 266, No. 22, pp. 14703-14708, (1991).

Perry, S.W, et al, "Simultaneous in situ detection of apoptosis and necrosis in monolayer cultures by TUNEL and trypan blue staining", Biotechniques, vol. 22, No. 6, pp. 1102-1106, (1997).

Pich, A, et al, "Prognostic relevance of AgNORs in tumor pathology", Micron, vol. 31, No. 2, pp. 133-141, (2000).

Pinton, P, et al, "The $Ca^{2+}$ concentration of the endoplasmic reticulum is a key determinant of ceramide-induced apoptosis: significance for the molecular mechanism of Bcl-2 action", EMBO J, vol. 20, pp. 2690-2701, (2001).

Platt, N, et al, "Recognizing death: the phagocytosis of apoptotic cells", Trends Cell Biology, vol. 8, No. 9, pp. 365-372, (1998).

Pleschke, J.M, et al, "Poly(ADP-ribose) binds to specific domains in DNA damage checkpoint proteins", J Biol Chem, vol. 275, No. 52, pp. 40974-40980, (2000).

Product Data Sheet for ab7898 from http://www.abcam.com/?datasheet=7898, (1998-2006).

Product Data Sheet for C23 (C-18): sc-9892, Santa Cruz Biotechnology, Inc, (2003).

Product Data Sheet for C23 (MS-3): sc-8031, Santa Cruz Biotechnology, Inc, (2004).

Product Data Sheet for C23 (F-18): sc-9893, Santa Cruz Biotechnology, Inc, (2003).

Product Data Sheet for p7-1A4, from http://dshb.biology.uiowa.edu/objects/catalog//product/extras/4217_p7- 1A4.pdf, Antibody Database Information, printed on Aug. 10, 2007.

Product Data Sheet for B23 (C-19): sc-6013, Santa Cruz Biotechnology, Inc., located at http://datasheets.scbt.com/sc-6013.pdf, printed on Aug. 10, 2007.

Product Data Sheet for B23 (H-106): sc-5564, Santa Cruz Biotechnology, Inc., located at http://datasheets.scbt.com/sc-5564.pdf, printed on Aug. 10, 2007.

Product Data Sheet for Monoclonal Antibody, Anti-Nucleolin M019-3, Medical & Biological Laboratories Co, LTD, www.mblintl.com, (2003).

Product Data Sheet for Anti-Nucleolin, Clone 3G4B2, Upstate Biotechnology, http://www.upstate.com/browse/productdetail.asp-?ProductId=05-565, (2005).

Puttaraju, M, et al, "Messenger RNA repair and restoration of protein function by spliceosome-mediated RNA trans-splicing", Mol Ther, vol. 4, No. 2, pp. 105-114, (2001).

Raab de Verdugo, U, et al, "Characterization of a 100-kilodalton binding protein for the six serotypes of coxsackie B viruses", Journal of Virology, vol. 69, No. 11, pp. 6751-6757, (1995).

Richardson, D.S, et al, "Effects of PARP inhibition on drug and Fas-induced apoptosis in leukaemic cells", Adv Exp Med Biol, vol. 457, pp. 267-279, (1999).

Robinson, J.M, et al, "Antigen retrieval in cells and tissues: enhancement with sodium dodecyl sulfate", Histochem Cell Biol, vol. 116, pp. 119-130, (2001).

Roninson, I.B, et al, "If not apoptosis, then what? Treatment-induced senescence and mitotic catastrophe in tumor cells", Drug Resist Update, vol. 4, No. 5, pp. 303-313, (2001).

Rosenthal, D.S, et al, "Detection of DNA breaks in apoptotic cells utilizing the DNA binding domain of poly(ADP-ribose) Polymerase with fluorescence microscopy", Nucleic Acids Research, vol. 25, No. 7, pp. 1437-1441, (1997).

Rothenburg, S, et al, "A polymorphic dinucleotide repeat in the rat nucleolin gene forms Z-DNA and inhibits promoter activity", PNAS, vol. 98, No. 16, pp. 8985-8990, (2001).

Roussel, P, et al, "Identification of Ag-NOR proteins, markers of proliferation related to ribosomal gene activity", Experimental Cell Research, vol. 214, No. 2, pp. 465-472, (1994).

Roussel, P, et al, "Quantification of Ag-NOR proteins using Ag-NOR staining on western blots", Histochem Cytochem, vol. 42, No. 11, pp. 1513-1517, (1994).

Saijo, Y, et al, "Contiguous four-guanosine sequence in c-myc antisense phosphorothioate oligonucleotides inhibits cell growth on human lung cancer cells: possible involvement of cell adhesion inhibition", Jpn J Cancer Research, vol. 88, No. 1, pp. 26-33, (1997).

Saikumar, P, et al, "Apoptosis: definition, mechanisms, and relevance to disease", Am J Med, vol. 107, No. 5, pp. 489-506, (1999).

Sandoval, A, et al, "Distal recognition site for classical pathway convertase located in the C345C/netrin module of complement component C5", J lmmunol, vol. 165, No. 2, pp. 1066-1073, (2000).

Schade, R, et al, "Egg yolk antibodies, State of the art and future prospects", Altex 13, supplement 96, pp. 5-9, (1996).

Schade, R, et al, "The production of avian (egg yolk) antibodies IgY. The report and recommendations of ECVAM workshop", Alternatives to laboratory animals (ATLA), vol. 24, pp. 925-934, (1996).

Schimmer, A.D, et al, "Receptor- and mitochondrial-mediated apoptosis in acute leukemia: a translational view", Blood, vol. 98, No. 13, pp. 3541-3553, (2001).

Schmidt-Acevedo, S, et al, "'LE cells' result from phagocytosis of apoptotic bodies induced by antinuclear antibodies", Journal of Autoimmunity, vol. 15, pp. 15-20, (2000).

Schmitt, C.A, et al, "Apoptosis is critical for drug response in vivo", Drug Resist Update, vol. 4, No. 2, pp. 132-134, (2001).

Sciavolino, P.J, et al, "Molecular biology of prostate development and prostate cancer", Ann Med, vol. 30, No. 4, pp. 357-368, (1998).

Scovassi, A.I, et al, "Poly(ADP-ribosylation) and apoptosis", Molecular and Cellular Biochemistry, vol. 199, pp. 125-137, (1999).

Semenkovich, C.F, et al, "A protein partially expressed on the surface of HepG2 cells that binds lipoproteins specifically is nucleolin", Biochemistry, vol. 29, No. 41, pp. 9708-9713, (1990).

Sen, D, et al, "Formation of parallel four-stranded complexes by guanine-rich motifs in DNA and its implications for meiosis", Nature, vol. 334, No. 6180, pp. 364-366, (1988).

Shall, S, et al, "Poly(ASP-ribose) polymerase-1: what have we learned from the deficient mouse model?", Mutat Research, vol. 460, No. 1, oo, 1-15, (2000).

Shall, S, "Poly (ADP-ribosylation)-a common control process?", Bioassays, vol. 24, No. 2, pp. 197-201, (2002).

Sharma, S, et al, "Development of inhalational agents for oncologic use", J Clin Oncol, vol. 19, No. 6, pp. 1839-1847, (2001).

Sharp, P.A, "RNA interference—2001" Genes Dev, vol. 15, No. 5, pp. 485-490, (2001).

Sharp, P.A, et al, "Molecular biology. RNA interference", Science, vol. 287, No. 5462, pp. 2431-2433, (2000).

Shaw, J.P, et al, "Modified deoxyoligonucleotides stable to exonuclease degradation in serum", Nucleic Acids Res, vol. 19, No. 4, pp. 747-750, (1991).

Sherwood, J.K. et al., "Controlled antibody delivery systems", Biotechnology, vol. 10, No. 11, pp. 1446-1449, (1992).

Shi, S.R, et al, "Antigen retrieval immunohistochemistry: past, present, and future", J Histochem Cytochem, vol. 45, pp. 327-343, (1997).

Shi, S.R, et al, "Antigen retrieval techniques: current perspectives", J Histochem Cytochem, vol. 49, pp. 931-937, (2001).

Shiokawa, D, et al, "Inhibitors of poly(ADP-ribose) polymerase suppress nuclear fragmentation and apoptotic-body formation during apoptosis in HL-60 cells", FEBS Letters, vol. 413, No. 1, pp. 99-103, (1997).

Simbulan-Rosenthal, C.M, et al, "Involvement of PARP and poly(ADP-ribosyl)ation in the early stages of apoptosis and DNA replication", Mol Cell Biochem, vol. 193, No. 1-2, pp. 137-148, (1999).

Sirri, V, et al, "Amount variability of total and individual Ag-NOR proteins in cells stimulated to proliferate", Histochem Cytochem, vol. 43, No. 9, pp. 887-893, (1995).

Skulstad, S, et al, "Labeling of surface proteins of herpes simplex virus type 1 using a modified biotin-streptavidin system", Virus Research, vol. 37, No. 3, pp. 253-270, (1995).

Smulson, M.E, et al, "Roles of poly(ADP-ribosyl)ation and PARP in apoptosis, DNA repair, genomic stability and functions of p53 and E2F-1", Adv Enzyme Regul, vol. 40, pp. 183-215, (2000).

Sohn, J.H, et al, "Caspase-3/CPP32 immunoreactivity and its correlation with frequency of apoptotic bodies in human prostatic carcinomas and benign nodular hyperplasias", Histopathology, vol. 37, No. 6, pp. 555-560, (2000).

Soldani, C. et al., "Poly(ADP-ribose) polymerase cleavage during apoptosis: when and where?", Exp Cell Research, vol. 269, No. 2, pp. 193-201, (2001).

Soldani, C. et al., "Two-color fluorescence detection of Poly (ADP-ribose) polymerase-1 (PARP-1) cleavage and DNA strand breaks in etoposide-induced apoptotic cells", Eur J Histochem, vol. 45, No. 4, pp. 389-392, (2001).

Sorokina, E.A, et al, "Cloning and preliminary characterization of a calcium-binding protein closely related to nucleolin on the apical surface of inner medullary collecting duct cells", J Biol Chem, vol. 274, No. 39, pp. 27491-27496, (1999).

Sperandio, S, et al, "An alternative, nonapoptotic form of programmed cell death", Proc Natl Acad Science USA, vol. 97, No. 26, pp. 14376-14381, (2000).

Srinivasan, S.K, et al, "Review of in vivo pharmacokinetics and toxicology of phosphorothioate oligonucleotides", J Clin Lab Anal, vol. 9, No. 2, pp. 129-137, (1995).

Srivastava, M, et al, "Molecular dissection of nucleolin's role in growth and cell proliferation: new insights", FASEB J, vol. 13, No. 14, pp. 1911-1922, (1999).

Stegh, A.H, et al, "DEDD, a novel death effector domain-containing protein, targeted to the nucleolus", EMBO J, vol. 17, No. 20, pp. 5974-5986, (1998).

Stein, C.A, "Is irrelevant cleavage the price of antisense efficacy?", Pharmacol Ther, vol. 85, No. 3, pp. 231-236, (2000).

Stein, C.A. "Keeping the biotechnology of antisense in context", Nat. Biotechnol, vol. 17, No. 3, pp. 209, (1999).

Stein, C.A, et al, "Phosphorothioate oligodeoxynucleotides-antisense inhibitors of gene expression?", Pharmacol Ther, vol. 52, No. 3, pp. 365-384, (1991).

Stone, K.R, et al, "Isolation of a human prostate carcinoma cell line (DU 145)", Int J Cancer, vol. 21, pp. 274-281, (1978).

Stroun, M, et al, "About the possible orgin and mechanism of circulating DNA apoptosis and active DNA release", Clin Chim Acta, vol. 313, No. 1-2, pp. 139-142, (2001).

Stryer, L, "Levels of structure in protein architecture", Biochemistry, Third Edition, chapter 2, pp. 31-33, W.H. Freeman Company, New York, (1988).

Summerton, J, et al, "Morpholino antisense oligomers: design, preparation, and properties", Antisense Nucleic Acid Drug Development, vol. 7, No. 3, pp. 187-195, (1997).

Sundquist, W.I, et al, "Telomeric DNA dimerizes by formation of guanine tetrads between hairpin loops", Nature, vol. 342, No. 6251, pp. 825-829, (1989).

Sundquist, W.I, et al, "Evidence for interstrand quadruplex formation in the dimerization of human immunodeficiency virus 1 genomic RNA", Proc Nati Acad Science USA, vol. 90, No. 8, pp. 3393-3397, (1993).

Sutton, V.R, et al, "Initiation of apoptosis by granzyme B requires direct cleavage of bid, but not direct granzyme B-mediated caspase activation", J Exp Med, vol. 192, No. 10, pp. 1403-1413, (2000).

Symons, R.H. "Small catalytic RNAs", Annual Review Biochem, vol. 61, pp. 641-671, (1992).

Takahashi, T, et al, "p53: a frequent target for genetic abnormalities in lung cancer", Science, vol. 246, pp. 491- 494, (1989).

Tanaka, Y, et al, "Inhibition and down-regulation of poly(ADP-ribose) polymerase results in a marked resistance of HL-60 cells to various apoptosis-inducers", Cell Mol Biol, vol. 41, No. 6, pp. 771-781, (1995).

Templin, M.V, et al, "Pharmacokinetic and toxicity profile of a phosphorothioate oligonucleotide following inhalation delivery to lung in mice", Antisense Nucleic Acid Drug Dev, vol. 10, No. 5, pp. 359-368, (2000).

Tentori, L, et al, "Potential clinical applications of poly(ADP-ribose) polymerase (PARP) inhibitors", Pharmacol Res, vol. 45, No. 2, pp. 73-85, (2002).

Thornberry, N.A, et al, "Caspases: enemies within", Science, vol. 281, pp. 1312-1316, (1998).

Tockman, M.S, et al, "Prospective detection of preclinical lung cancer: results from two studies of heterogeneous nuclear ribonucleoprotein A2/B1 overexpression", Clin Cancer Research, vol. 3, No. 12, pt. 1, pp. 2237-2246, (1997).

Tockman, M.S, et al, "Sensitive and specific monoclonal antibody recognition of human lung cancer antigen on preserved sputum cells: a new approach to early lung cancer detection", J Clin Oncol, vol. 6, No. 11, pp. 1685-1693, (1988).

Tormanen, U, et al, "Enhanced apoptosis predicts shortened survival in non-small cell lung carcinoma", Cancer Research, vol. 55, No. 23, pp. 5595- 5602, (1995).

Trere, D, "AgNOR staining and quantification", Micron, vol. 31, No. 2, pp. 127-131, (2000).

Tu, G.C, et al, "Tetranucleotide GGGA motif in primary RNA transcripts. Novel target site for antisense design", J Biol Chem, vol. 273, No. 39, pp. 25125-25131, (1998).

Tuteja, N, et al, "Human DNA helicase IV is nucleolin, an RNA helicase modulated by phosphorylation", Gene, vol. 160, No. 2, pp. 143-148, (1995).

Tuteja, R, et al, "Nucleolin: a multifunctional major nucleolar phosphoprotein", Crit Rrev Biochem Mol Biol, vol. 33, pp. 407-436, (1998).

van de Loosdrecht, A.A, et al, "A tetrazolium-based colorimetric MTT assay to quantitate human monocyte mediated cytotoxicity against leukemic cells from cell lines and patients with acute myeloid leukemia", J Immunol Methods, vol. 174, pp. 311-320, (1994).

Waggoner, S, et al, "Viral ribonucleoprotein complex formation and nucleolar-cytoplasmic relocalization of nucleolin in poliovirus-infected cells", J Virol, vol. 72, No. 8, pp. 6699-6709, (1998).

Wang, W, et al, "A comparison of guanosine-quartet inhibitory effects versus cytidine homopolymer inhibitory effects on rat neointimal formation", Antisense Nucleic Acid Drug Development, vol. 8, No. 3, pp. 227-236, (1998).

Wang, Y, et al, "Regulation of dna replication after heat shock by replication protein a-nucleolin interactions", J Biol Chem, vol. 276, No. 23, pp. 20579-20588, (2001).

Wang, Y, et al, "Solution structure of the human telomeric repeat d[AG3(T2AG3)3] G-tetraplex", Structure, vol. 1, No. 4, pp. 263-282, (1993).

Wang, Z.Q, et al, "PARP is important for genomic stability but dispensable in apoptosis", Genes Dev, vol. 11, No. 18, pp. 2347-2358, (1997).

Weisenberger, D, et al, "A possible mechanism for the inhibition of ribosomal RNA gene transcription furing mitosis", J Cell Biology, vol. 129, No. 3, pp. 561-575, (1995).

White, J.R, et al, "Phosphorothioate-capped antisense oligonucleotides to Ras GAP injibit cell proliferation and trigger apoptosis but fail to downregulate GAP gene expression", Biochem Biophys Res Commun, vol. 227, No. 1, pp. 118-124, (1996).

Whittles, C.E, et al, "Apoptotic and proliferative activity in the neoplastic progression of Barrett's oesophagus: a comparative study", The Journal of Pathology, vol. 187, issue 5, pp. 535-540, (1999).

Williamson, J.R, et al, "Monovalent cation-induced structure of telomeric DNA: the G-quartet model", Cell, vol. 59, No. 5, pp. 871-880, (1989).

Winter, G, et al, "Making antibodies by phage display technology", Annu Rev Immunol, vol. 12, pp. 433-455, (1994).

Wolters, D.A, et al, "An automated multidimensional protein identification technology for shotfun proteomics", Anal Chem, vol. 73, No. 23, pp. 5683-5690, (2001).

Wurzer, G, et al, "Increased resistance to anticancer therapy of mouse cells lacking the poly(ADP-ribose) polymerase attributable to up-regulation of the multidrug resistance gene product P-glycoprotein", Cancer Research, vol. 60, No. 15, pp. 4238-4244, (2000).

Wyatt, J.R, et al, "Combinatorially selected guanosine-quartet structure is a potent inhibitor of human immunodeficiency virus envelope-mediated cell fusion", Proc Natl Acad Science USA, vol. 91, No. 4, pp. 1356-1360, (1994).

Wyllie, A.H, et al, "Cell death: the significance of apoptosis", International Review of Cytology, vol. 68, pp. 251-306, (1980).

Wysocki, L.J, et al, ""Panning" for lymphocytes: a method for cell selection", Proc Natl Acad Sci USA, vol. 75, No. 6, pp. 2844-2848, (1978).

Xu, X, et al, "Inhibition of DNA replication and induction of S phase cell cycle arrest by G-rich oligonucleotides", The Journal of Biological Chemistry, vol. 276, No. 46, pp. 43221-43230, (2001).

Xue, Z, et al, "The amino terminus of mammalian nucleolin specifically recognizes SV40 T-antigen type nuclear localization sequences", Eur J Cell Biol, vol. 62, No. 1, pp. 13-21, (1993).

Yanagida, M, et al, "Isolation and proteomic characterization of the major proteins of the nucleolin-binding ribonucleoprotein complexes", Proteomics, vol. 1, No. 11, pp. 1390-1404, (2001).

Yao, G.Q, et al, "Identification of two oligodeoxyribonucleotide binding proteins on plasma membranes of human cell lines", Biochemical Pharmacology, vol. 51, pp. 431-436, (1996).

Xiao-Ming, Y., "Signal transduction mediated by Bid, a pro-death Bcl-2 family proteins, connects the death receptor and mitochondria apoptosis pathways", Cell Research, vol. 10, No. 3, pp. 161-167, (2000).

European Search Report dated Oct. 25, 2006 for European application No. 03762073.9.

Mi, Y., et al., "Apoptosis in Leukemia cells is accompanied by alterations in the levels and localization of Nucleolin", The Journal of Biological Chemistry, vol. 278, No. 10, pp. 8572-8579, (2003).

Rosen, A., et al., "Autoantigens as substrates for apoptotic proteases: implications for the pathogenesis of systemic autoimmune disease", Cell Death and Differentiation, vol. 6, No. 1, pp. 6-12, (1999).

Masters, J.R.W., "Human cancer cell lines: fact and fantasy", Nature Reviews Molecular Cell Biology, vol. 1, pp. 233-236, (2000).

Mi, Y. et al., "Regulation of Nucleolin in U937 Cells Treated with UV-Light and Cytotoxic Drugs", Blood, vol. 98, No. 11, Part 2 of 2, Abstract No. 4223, (2001).

Destouches, D. et al., "Suppression of tumor growth and angiogenesis by a specific antagonist of the cell-surface expressed nucleolin", Plos One, vol. 3, issue 6, e2518, pp. 1-12, (2008).

Fogal, V. et al., "Cell surface nucleolin antagonist causes endothelial cell apoptosis and normalization of tumor vasculature", Angiogenesis, vol. 12, No. 1, pp. 91-100, (2009).

Ugrinova I. et al., "Inactivation of nucleolin leads to nucleolar disruption, cell cycle arrest and defects in centrosome duplication", BMC Molecular Biology, pp. 1-16, (2007).

Cylene Pharmaceuticals, Quarfloxin Nucleolus Targeting Agent (CX-3543), Quarfloxin QPLX/Nucleolin Inhibitor (CX-3543), 1 page, printed on Jan. 21, 2010.

ImmuPharma, Treatment for Cancer (IPP-204106), pp. 1-3, found at http://immupharma.com/cancer.html, printed on Jan. 21, 2010.

Invitation to Pay Additional Fees and International Fees and Partial Search Report dated Jul. 14, 2009 for PCT/US2008/088491.

Grinstein, E. et al., "Cellular signaling in normal and cancerous stem cells", Cellular Signaling, 19, pp. 2428-2433, (2007).

Grinstein, E. et al., "Nucleolin Regulates Gene Expression in CD34-positive Hematopoietic Cells", The Journal of Biological Chemistry, vol. 282, No. 17, pp. 12439-12449, (2007).

Soltysova, A. et al., "Cancer Stem Cells", Neoplasma, 52, 6, pp. 435-440, (2005).

Huang, E.H. et al., "Cancer stem cells: A new paradigm for understanding tumor progression and therapeutic resistance", Surgery, vol. 141, pp. 415-419, (2007).

Girvan, A.C. et al., "AGRO100 inhibits activation of nuclear factor-κb (NF-κB) by forming a complex with NF-κB essential modulator (NEMO) and nucleolin", Molecular Cancer Therapeutics, vol. 5, No. 7, pp. 1790-1799, (2006).

Christian, S. et al., "Nucleolin expressed at the cell surface is a marker of endothelial cells in angiogenic blood vessels", The Journal of Cell Biology, vol. 163, No. 4, pp. 871-878, (2003).

Clarke. M.F. et al., "Stem Cells: The Real Culprits in Cancer?", Scientific American, 295, 1, pp. 52-59, (2006).

* cited by examiner

```
                         SEQUENCE LISTING

<160> NUMBER OF SEQ ID NOS: 38

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 1
tttggtggtg gtggttgtgg tggtggtgg                                            29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 2
tttggtggtg gtggttttgg tggtggtgg                                            29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 3
tttggtggtg gtggtggtgg tggtggtgg                                            29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 4
tttggtggtg gtggtttggg tggtggtgg                                            29

<210> SEQ ID NO 5
<211> LENGTH: 13
```

```
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 5
tggtggtggt ggt                                                          13

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 6
ggtggttgtg gtgg                                                         14

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 7
gttgtttggg gtggt                                                        15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 8 ttggggggggg tgggt                                                       15

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 9
ggttggggtg ggtggggtgg gtggg                                             25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 10
ggtggtggtg gttgtggtgg tggtgg                                            26

<210> SEQ ID NO 11
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      polynucleotide sequence

<400> SEQUENCE: 11
tttggtggtg gtggttgtgg tggtggtg                                            28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 12
tttggtggtg gtggtgtggt ggtggtgg                                            28

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 13
ggtggtggtg gttgtggtgg tggtggttt                                           29

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 14
ggtggttgtg gtggttgtgg tggttgtggt gg                                       32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 15
tttggtggtg gtggttgtgg tggtggtggt tt                                       32

<210> SEQ ID NO 16
<211> LENGTH: 56
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 16
ggtggtggtg gttgtggtgg tggtggttgt ggtggtggtg gttgtggtgg tggtgg             56

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
```

-continued polynucleotide sequence

<400> SEQUENCE: 17
tcgagaaaaa ctctcctctc cttccttcct ctcca                35

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 18
tttcctcctc ctccttctcc tcctcctcc                29

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 19
ttagggttag ggttagggtt aggg                24

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 20
ggtggtggtg g                11

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 21
ggtggttgtg gtgg                14

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 22
ggttggtgtg gttgg                15

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      polynucleotide sequence

```
<400> SEQUENCE: 23
gggttttggg                                                          10

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 24
ggttttggtt ttggttttgg                                               20

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 25
ggttggtgtg gttgg                                                    15

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 26
ggggttttgg gg                                                       12

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 27
gggttttggg                                                          10

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 28
ggggttttgg ggttttgggg ttttgggg                                      28

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 29
```

```
ttggggttgg ggttgggtt gggg                                         24
```

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 30

```
gggtgggtgg gtgggt                                                 16
```

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 31

```
ggttttggtt ttggttttgg ttttgg                                      26
```

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 32

```
tttcctcctc ctccttctcc tcctcctcc                                   29
```

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 33

```
cctcctcctc cttctcctcc tcctcc                                      26
```

<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 34

```
tggggt                                                             6
```

<210> SEQ ID NO 35
<211> LENGTH: 7
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 35

```
gcatgct                                                            7
```

```
-continued

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 36
gcggtttgcg g                                                              11

<210> SEQ ID NO 37
<211> LENGTH: 4
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 37 tagg                                                                       4

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 38
ggggttgggg tgtggggttg ggg                                                 23
```

METHOD FOR THE DIAGNOSIS AND PROGNOSIS OF MALIGNANT DISEASES

RELATED APPLICATION

This application is a continuation of U.S. patent application Ser. No. 10/683,480, filed Oct. 9, 2003 (now U.S. Pat. No. 7,357,928) which is a continuation-in-part of U.S. application Ser. No. 10/118,854, filed Apr. 8, 2002 now U.S. Pat. No. 7,541,150, which is herein incorporated by reference in its entirety.

BACKGROUND

Cancer

Being well-prepared for battle engenders success; when the foe is cancer, early detection results in a greater likelihood that medical intervention will be successful. At early stages, treatments can often be targeted only to the affected tissues, diminishing side effects. If not caught early, cancer cells may metastasize and spread throughout the body. The prognosis in this case is more dire, and medical treatments are often applied systemically, killing not only cancer cells, but large numbers of healthy cells.

The National Cancer Institute estimates that in 2002, 1.285 million Americans will be newly diagnosed with cancer, and more than 560,000 Americans will die from of cancer related illness.

A hallmark of a cancer cell is uncontrolled proliferation. Uncontrolled proliferation of these cells can manifest as cell masses (tumors) that interfere with normal organ function. If proliferation is not controlled or contained, cells from tumors migrate and colonize other tissues of the body, eventually resulting in death.

External factors, such as tobacco smoke, radiation and viruses, can lead to alterations in specific genes that result in unregulated cellular proliferation. Intrinsic factors, including inheritable mutations, hormone levels and metabolism, contribute to one's risk of contracting cancer.

Cancer cells also exhibit morphological and functional aberrations. Cellular morphology may be less organized; for example, the cells losing the asymmetric organelle and structural organization (cell polarity) that allows for proper cell function. Cell-cell and cell-substratum contacts, the specificities of which are also necessary for normal function, are often modulated or lost. Functionally, the cells may carry on few, if any, wild-type functions, or may have exaggerated, unregulated normal functions, such as hormone secretion. Such cells regress to early developmental stages, appearing less differentiated than their wild-type (i.e., normal) parents.

Cancer cells also often mis-express or mis-target proteins to inappropriate cellular compartments. Proteins may be up- or down-regulated; even proteins not usually expressed by a specific cell type can be expressed by the transformed counterpart. Protein mis-expression can have a plethora of downstream cellular effects, including drastic changes in membrane composition, organelle formation, or physiology. Mis-targeting of proteins (and other molecules, such as lipids, etc.) also contributes to the loss of cell polarity.

Treatments for Cancer

Methods for treating cancers include surgery (physical removal of the cancerous tissues), radiation therapy (killing cells by exposure to cell-lethal doses of radioactivity), chemotherapy (administering chemical toxins to the cells), immunotherapy (using antibodies that target cancer cells and mark them for destruction by the innate immune system) and nucleic acid-based therapies (e.g., expression of genetic material to inhibit cancer growth). Each approach, however, has its limitations.

Surgery, chemotherapy and radiation therapy suffer from similar significant limitations, such as incomplete removal of cancer cells or the inadvertent killing of healthy cells. Surgical tactics are most effective when the cancers are in early stages and limited localized area in the body. Even in the few cases that are diagnosed early, surgical removal of cancerous cells is often incomplete, and re-emergence of metastatic lesions often follow. When chemotherapeutic agents are administered in precise doses, they are preferentially toxic to rapidly proliferating cancer cells and not injuring the majority of healthy cells. Locally delivered doses of external beam radiation are most effective on rapidly growing cells, killing them by introducing non-specific, DNA-damage. Radiation therapy, like surgery, works best when the targeted cancer mass is well delimited; the balance of killing healthy cells versus cancer cells must be carefully weighed. Both chemotherapy and radiation therapy are not entirely selective for cancerous cells; inevitably, some healthy cells fall victim to the toxic effects, inflicting profound side-effects on the already-suffering cancer victim.

Other common approaches, immunotherapy and gene therapy, can be quite powerful and surpass surgery, chemo- and radiation therapy. These techniques target specific factors that are associated with tumor survival, cell growth or metastasis. For example, antibodies can target specific tumor-associated proteins, such as the monoclonal antibody that binds to a surface protein specific to the B-cells, CD20 (RITUXAN®; Genentech, Inc. and IDEC Inc.) that is used to treat B-cell malignancies. An example of an effective gene therapy is anti-sense inhibition of bcl-2 expression (GENASENSE®; Genta, Inc.). While effective, the challenge is to identify those clinically relevant genes and proteins and develop appropriate therapeutics that target them to result in the destruction of the cancer cell. Furthermore, the process is not only laborious in identifying these molecules, but in many instances, the identified molecules will be specific to only one type of cancer or tumor cell.

SUMMARY

The invention provides methods for treating tumors or cancer in a subject by:

(1) administering a therapeutically effective amount of an anti-nucleolin agent and a pharmaceutically acceptable carrier. This pharmaceutical composition may further comprise other chemotherapeutic or chemotoxic agents, such as cyclophosphamide, etoposide, doxorubicin, methotrexate, vincristine, procabazine, prednizone, dexamethasone, tamoxifen citrate, carboplatin, cisplatin, oxaliplatin, 5-fluorouracil, camptothecin, zoledronic acid, Ibandronate and mytomycin. In conjunction, radiation therapy may also be plied.

(2) administering a therapeutically effective amount of an anti-nucleolin antibody and a pharmaceutically acceptable carrier, wherein the antibody is substantially non-immunogenic to human. This pharmaceutical composition may further comprise other chemotherapeutic or chemotoxic agents. In conjunction, radiation therapy may also be plied.

(3) administering a therapeutically effective amount of an anti-nucleolin antibody, a chemotoxic or chemotherapeutic agent and a pharmaceutically acceptable carrier.

(4) administering a therapeutically effective amount of a nucleolin antibody and a pharmaceutically acceptable carrier, and further treating the subject with radiation therapy.

(5) administering a therapeutically effective amount of a duplex interfering RNA to nucleolin and a pharmaceutically acceptable carrier.

(6) administering a nucleolin anti-sense molecule which inhibits the production of the nucleolin protein.

(7) administering a nucleolin-interfering RNA molecule which inhibits the expression of the nucleolin gene.

In these aspects, a chemotherapeutic or chemotoxic agent may be cyclophosphamide, etoposide, doxorubicin, methotrexate, vincristine, procabazine, prednizone, dexamethasone, tamoxifen citrate, carboplatin, cisplatin, oxaliplatin, 5-fluorouracil, camptothecin, zoledronic acid, Ibandronate and mytomycin.

In yet another aspect, the invention provides pharmaceutical compositions that comprise a pharmaceutically acceptable carrier and:

(8) an anti-sense oligonucleotide directed against nucleolin.

(9) an inhibitory RNA against nucleolin.

(10) a nucleolin antibody.

DETAILED DESCRIPTION

Figure 1:
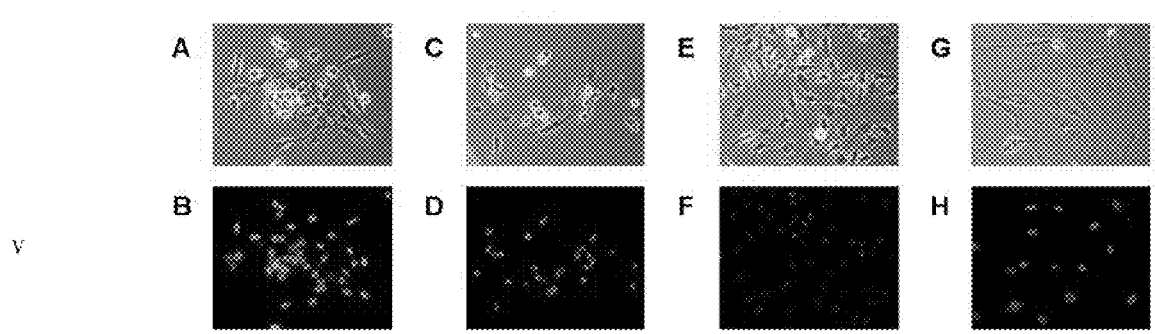
FIG. 1 shows nuclear nucleolin staining in various cell lines. Shown are immunofluorescent (B, D, F, H) and parallel phase contrast micrographs (A, C, E, G). Cell lines that were analyzed were: DU145 prostate cancer cells (A, B), MDA-MB-231 breast cancer cells (C, D), HeLa cervical cancer cells (E, F) and HS27 normal skin cells (G, H). An anti-nucleolin antibody was used; the cells were permeabilized before staining to allow the antibody access to the cytoplasmic and nuclear compartments.

The invention is based on the discovery of a correlation between nucleolin plasma membrane expression and the presence and aggressiveness of neoplastic cells. The unexpected discovery that nucleolin, mostly restricted to the interior of the healthy cell nucleus, when found on the cell surface, correlates with a pre-malignant or malignant phenotype. Not only does this observation facilitate cancer diagnosis and prognosis, but also provides a novel and powerful treatment strategy. The invention provides methods of treating cancer by administering a compound that specifically targets nucleolin. Furthermore, the invention provides methods for treating cancer by administering a nucleolin-targeting compound in conjunction with other cancer therapies, e.g., an anti-cancer drug. Such combination therapy achieves superior and synergistic therapeutic results.

The advantages of using surface-localized nucleolin to treat tumors and cancers include:

(1) Specificity. Plasma membrane nucleolin is not usually observed in the plasma membrane of most wild-type (healthy) cells. Thus, unlike other non-specific therapeutic approaches (e.g., surgery, radiation, chemotoxins), plasma membrane nucleolin targeting can be used to specifically kill cancer cells.

(2) Broad applicability. Unlike previous immuno- and gene therapies, nucleolin expression on the plasma membrane occurs on many types of cancer cells. Many different cancers, therefore, may be treated by exploiting plasma membrane nucleolin; yet, unlike other less-specific treatments (e.g., radiation therapy), healthy cells are not damaged or killed.

(3) Treatment: early or late. Because plasma membrane nucleolin is indicative of not only malignant cells, but also of pre-malignant cells, treatment can commence with the detection of surface nucleolin, even before a tumor mass would usually be detected by other means.

While investigating the anti-proliferative activity of non-anti-sense guanosine-rich oligonucleotides (GROs) on cancer cells, it was found that such anti-proliferative GROs bind nucleolin to exert their effects (Bates et al., 1999; Miller et al., 2000). Nucleolin (Bandman et al., 1999) is an abundant, non-ribosomal protein of the nucleolus, the site of ribosomal gene transcription and packaging of pre-ribosomal RNA. This 707 amino acid phosphoprotein has a multi-domain structure consisting of a histone-like N-terminus, a central domain containing four RNA recognition motifs and a glycine/arginine-rich C-terminus and has an apparent molecular weight of 110 kD. Its multiple domain structure reflects the remarkably diverse functions of this multifaceted protein (Ginisty et al., 1999; Srivastava and Pollard, 1999; Tuteja and Tuteja, 1998). Nucleolin has been implicated in many fundamental aspects of cell survival and proliferation. Most understood is the role of nucleolin in ribosome biogenesis. Other functions may include nucleocytoplasmic transport, cytokinesis, nucleogenesis and apoptosis. Nucleolin is one of the nuclear organizer region (NOR) proteins whose levels, as measured by silver staining, are assessed by pathologists as a marker of cell proliferation and an indicator of malignancy (Derenzini, 2000).

Also present in the cell plasma membrane in a few cell types, such as lymphocytes and inner medullary collecting duct cells, nucleolin has been hypothesized to function as a receptor (e.g., (Callebaut et al., 1998; Sorokina and Kleinman, 1999). However, the role of plasma membrane nucleolin is not well understood. In addition, it is not clear whether the plasma membrane nucleolin is identical to the nucleolar protein, or if it represents a different isoform or nucleolin-like protein. However, the expression of plasma membrane nucleolin is specific to neoplastic cells (such as malignant or pre-malignant); thus the function of plasma membrane nucleolin need not be known for effective therapeutic intervention.

DEFINITIONS

Neoplasm, Malignancy, Tumor, Cancer Cells

A neoplasm is an abnormal tissue growth resulting from neoplastic cells, cells that proliferate more rapidly and uncontrollably than normal cells. Usually partially or completely structurally disorganized, neoplasms lack functional coordination with the corresponding normal tissue. Neoplasms usually form a distinct tissue mass that may be either benign (tumor) or malignant (cancer).

Cancer cells invade surrounding tissues, may metastasize to distant sites, and are likely to recur after attempted removal, causing death of a subject if not adequately treated. In addition to structural disorganization, cancer cells usually regress to more primitive or undifferentiated states (anaplasia), although morphologically and biochemically, they may still exhibit many functions of the corresponding wild-type cells. Carcinomas are cancers derived from epithelia; sarcomas are derived from connective tissues. In some cases, cancers may not be associated with a tumor, but like the affected tissue, is defuse, e.g., leukemias.

Cancers may be more aggressive or less aggressive. The aggressive phenotype of a cancer cell refers to the proliferation rate and the ability to form tumors and metastasize in nude mice. Aggressive cancers proliferate more quickly, more easily form tumors and metastasize than less-aggressive tumors.

Tumors and cancers include solid, dysproliferative tissue changes and diffuse tumors. In the sense that cancers and tumors are abnormal growths having uncontrolled proliferation of cells that do not serve a normal physiological function, the terms "tumor" and "cancer" are used interchangeably. Examples of tumors and cancers include melanoma, lymphoma, plasmocytoma, sarcoma, glioma, thymoma, leukemia, breast cancer, prostate cancer, colon cancer, liver cancer, esophageal cancer, brain cancer, lung cancer, ovary cancer, cervical cancer, hepatoma, and other neoplasms. For more examples of tumors and cancers, see, for example (Stedman, 2000).

"Stromal cells" are accessory cells found within a tumor. Such cells may be, for example, fibroblasts, reticular cells and endothelial cells, and play a supportive role in tumor growth but are healthy cells. Stromal cells and fibroblasts therefore are constituents of the micro-environment in which tumor cells invade during metastasis.

Neoplastic State

The term "neoplastic state" refers to three conditions: normal, pre-malignant and malignant. "Normal" refers to a growth or cell that is clinically normal (healthy). "Pre-malignant" refers to a growth or cell that is on the pathway to malignancy, but at the time of examination, would not be classified as malignant by conventional methods. "Malignant" refers to a cell or growth that has at least one of the following properties: locally invasive, destructive growth and metastasis.

GROs and Other Polypeptide-Binding Oligonucleotides

Oligonucleotides are available that specifically bind to polypeptides, such as nucleolins. Examples of such are GROs, which are guanosine-rich oligonucleotides. Characteristics of GROs include:

(1) having at least 1 GGT motif
(2) preferably having 4-100 nucleotides, although GROs having many more nucleotides are possible
(3) having chemical modifications to improve stability.

Especially useful GROs form G-quartet structures, as indicated by a reversible thermal denaturation/renaturation profile at 295 nm (Bates et al., 1999). Preferred GROs also compete with a telomere oligonucleotide for binding to a target cellular protein in an electrophoretic mobility shift assay (Bates et al., 1999).

Other oligonucleotides may have high binding specificity for nucleolin.

Anti-Nucleolin Agent

An "anti-nucleolin agent" binds to nucleolin. Examples include anti-nucleolin antibodies and certain oligonucleotides.

Nucleic Acid-Based Definitions

A "structural gene" or "gene" refers to a DNA sequence that is transcribed into messenger RNA (mRNA) which can be translated into a polypeptide (a polypeptide consists of at least two amino acid residues).

A promoter is a DNA sequence that specifies the site of initiation of RNA transcription, the direction of transcription, and the rate of transcription. For this reason, promoters are usually located 5' of the start site (designated as +1) for the DNA sequence that encodes the resultant RNA transcript. Promoters can be unregulated or regulated. When a promoter is unregulated, it operates constitutively at a particular basal level of activity. When the promoter is regulated, the efficiency of a promoter can be modulated in response to an agent. RNA transcription is increased relative to the basal transcription level under circumstances where an agent positively regulates promoter activity; conversely, RNA transcription is decreased relative to the basal transcription level under circumstances where an agent negatively regulates promoter activity. Agents that positively regulate promoter activity are called activators; whereas agents that negatively regulate promoter activity are called repressors.

An enhancer is a DNA transcription element that can increase the efficiency of promoter activity. Like promoters, enhancers are physically linked to the affected gene. Enhancers may also be unregulated or regulated. Unlike promoters, however, enhancers cannot specify the start site of RNA transcription or the direction of transcription. Enhancers can stimulate gene expression independent of the enhancer's orientation and location with respect to the start site of RNA transcription. Because enhancers do not specify the start site of RNA transcription, enhancers can exert their effects over great distances (several kilobases) with respect to a particular gene.

A regulatory sequence is typically a short DNA motif that positively or negatively responds to the activity of an agent. A regulatory sequence may be bidirectional or unidirectional. A regulatory sequence can be part of the modular organization of either a promoter or an enhancer. In the context of a promoter, a regulatory sequence either modulates promoter efficiency and/or affects the selection of initiation sites of RNA transcription. In the context of an enhancer, a regulatory sequence modulates the efficiency of an enhancer.

A "cloning vector" is a DNA molecule such as a plasmid, cosmid, or bacteriophage that has the ability to replicate in a cell. Cloning vectors typically contain restriction endonuclease recognition sites that enable the introduction of changes and additions of DNA fragments. Cloning vectors also typically include promoters to enable efficient expression and selectable markers that confer resistance to compounds such as ampicillin or tetracycline.

An "expression vector" is a polynucleotide comprising a coding sequence (such as a gene) that is made to be expressed by the host cell. Expression vectors typically contain promoters, enhancers and tissue specific regulatory elements that are operably linked to the expressed gene or DNA fragment.

The term "isoform" refers to polypeptides that differ in amino acid sequence or post-translational modifications (such as glycosylation or proteolytic processing events). Isoforms are also used to refer to polypeptides arising from a common gene which result from alternative splicing.

Therapy-Related Definitions

"Cytotoxic agent" refers to a substance that inhibits or prevents at least one function of a cell, or causes the destruction of a cell. Radioactive isotopes (e.g., $^{211}$At, $^{90}$Y, $^{186}$Re, $^{188}$Re, $^{153}$Sm, $^{212}$Bi, $^{32}$P and radioactive isotopes of Lu), and chemotherapeutic agents and toxins, such as small molecule toxins, or toxins from bacteria, fungi, plants or animals are examples of such agents.

"Radiation therapy" and "radiotherapy" refers to the use of locally delivered doses of external beam radiation to effect killing of a tumor or cancer cell.

A "chemotherapeutic agent" is a chemical compound that can be used effectively to treat a cancer cell. Examples of commonly used oncology drugs and agents include vinorelbine (Navelbine®), mytomycin, camptothecin, cyclyphosphamide (Cytoxin®), methotrexate, tamoxifen citrate, 5-fluorouracil, irinotecan, doxorubicin, flutamide, paclitaxel (Taxol®), docetaxel, vinblastine, imatinib mesylate (Gleevec®), anthracycline, letrozole, arsenic trioxide (Trisenox®), anastrozole, triptorelin pamoate, ozogamicin, irinotecan hydrochloride (Camptosar®), BCG, live (Pacis®), leuprolide acetate implant (Viadur), bexarotene (Targretin®), exemestane (Aromasin®), topotecan hydrochloride (Hycamtin®), gemcitabine HCL (Gemzar®), daunorubicin hydrochloride (Daunorubicin HCL®), gemcitabine HCL (Gemzar®), toremifene citrate (Fareston), carboplatin (Paraplatin®), cisplatin (Platinol® and Platinol-AQ®) oxaliplatin and any other platinum-containing oncology drug.

"Medicament," "therapeutic composition" and "pharmaceutical composition" are used interchangeably to indicate a compound, matter, mixture or preparation that exerts a therapeutic effect in a subject.

"Approved therapeutic antibodies" include rituximab (Rituxan®), gemtuzumab (Mylotarg®), alemtuzumab (Campath®) and trastuzumab (Herceptin®).

"Antibody" is used in the broadest sense and refers to monoclonal antibodies, polyclonal antibodies, multispecific antibodies, antibody fragments and derivatives.

An "artificial antibody" is a binding agent having polypeptide binding domains connected to polypeptide scaffolds (Irving et al., 2001; Koide, 2002).

A "conjugated antibody drug" refers to a therapeutic agent which includes an antibody or antibody fragment which is conjugated to a moiety that is a cytotoxic agent.

An "antibody fusion protein" refers to a recombinant molecule that comprises one or more antibody components and a therapeutic agent such as a cytokine, enzyme or a cytotoxic agent.

The term "naked antibody" refers to an entire, intact antibody, such as a monoclonal, recombinant monoclonal or polyclonal antibody that is neither fused nor conjugated to an enzyme, cytotoxic agent or chemotherapeutic agent.

A "nucleolin antibody" or "anti-nucleolin antibody" is an antibody, conjugated antibody drug, antibody fusion protein, naked antibody or artificial antibody that binds to nucleolin polypeptides.

"Anti-sense oligonucleotides," "oligo," "oligo nucleic acid," "anti-sense," or "anti-sense polynucleotide" are sequence-specific drugs capable of selectively modifying or silencing the expression of genes, causing a desired therapeutic effect.

The term "interfering RNA," "RNAi," "short interfering RNA" or "double stranded interfering RNA" refer to either free ribonucleic acid molecules or those generated in vivo by means of gene expression systems. Such interfering RNA molecules are able to alter the expression of a target gene.

"Treating a tumor" or "treating a cancer" means to significantly inhibit tumor/cancer growth and/or metastasis. Growth inhibition can be indicated by reduced tumor volume or reduced occurrences of metastasis. Tumor growth can be determined, e.g., by examining the tumor volume via routine procedures (such as obtaining two-dimensional measurements with a dial caliper). Metastasis can be determined by inspecting for tumor cells in secondary sites or examining the metastatic potential of biopsied tumor cells in vitro using well-known techniques.

An "anti-nucleolin agent" includes any molecule, compound, etc., that interacts with nucleolin. Such agents include anti-nucleolin antibodies and derivatives thereof, anti-sense oligonucleotides, ribozymes, RNAi, etc.

EMBODIMENTS

The following embodiments are given as examples of various ways to practice the invention. Many different ways of practicing the invention are also possible.

In all embodiments, the underlying principle is to target cells for therapeutic invention by specifically differentiating between plasma membrane nucleolin and nuclear nucleolin. Plasma membrane nucleolin, as discovered by the applicants, correlates with cells that are in a neoplastic state. Exploiting this differential plasma membrane expression, tumor and cancer cells can be targeted for treatment.

Detection of Plasma Membrane Nucleolin

Various techniques allow a user to differentiate between nuclear and plasma membrane nucleolin. Detection techniques, wherein the nucleolin-detecting reagents have exclusive access to extracellular portions of the cell (and consequently cell-plasma membrane nucleolin), or biochemical techniques, wherein either the surface plasma membrane and/or surface proteins are separated from other cellular components and compartments, are also useful. One practicing the invention may wish to determine the potential effectiveness of a therapy targeting nucleolin by first examining the cells for nucleolin plasma membrane expression.

In an embodiment, nucleolin is detected directly on the cell surface. A cell is isolated from a subject and plasma membrane nucleolin detected using an agent that binds nucleolin. Cells may be isolated by any known technique. An isolated cell may comprise a larger tissue sample containing cells that are not neoplastic. Detection procedures use anti-nucleolin antibodies that bind extracellular nucleolin epitopes; these antibodies may be directly labeled or when bound, detected indirectly. Other useful plasma membrane nucleolin detection agents include GROs that specifically bind nucleolin. Useful procedures, such as fluorescence-activated cell sorting (FACS) or immunofluorescence, employ fluorescent labels, while other cytological techniques, such as histochemical, immunohistochemical and other microscopic (electron microscopy (EM), immuno-EM) techniques use various other labels, either calorimetric or radioactive. The various reagents may be assembled into kits.

In another embodiment, cells are isolated from a subject and extracted. Plasma membranes and/or proteins are then isolated (such as via differential extraction, or differential physical cell disruption, differential centrifugation of detergent-extracted cells, etc.), and then nucleolin detected in the isolated membranes using an agent that binds nucleolin. In general, useful techniques to detect nucleolin include those wherein the extract is placed on a substrate, and the substrate probed with a nucleolin-detecting reagent. Examples of such techniques include polypeptide dot blots and Western blots, biochips, protein arrays, etc. Other detection formats include enzyme-linked immunosorbent assays (ELISAs) in their manifold manifestations (Ausubel et al., 1987). In embodiments wherein plasma membrane surface molecules are physically separated from most of the other cellular components and compartments, the nucleolin-binding agents need not specifically recognize any extracellular portions of nucleolin. The various reagents may be assembled into kits.

In a further embodiment, the methods of the invention are directed to detecting lung cancer, such as lung small cell carcinomas. Plasma membrane nucleolin expression is useful for detection and prognosis.

In one embodiment, the invention provides a method for the identification of a subject for whom a certain therapy, such as nucleolin-directed chemotherapy, is indicated for the treatment or amelioration of a condition associated with an increased abundance of nucleolin on the cell surface. Such a condition includes cancer, neoplasia and a precancerous lesion. Such a method may include the steps of contacting an agent that binds specifically to nucleolin with a cell in or from a subject and determining the amount of binding of plasma membrane nucleolin.

In another embodiment, an individual who has, in the past, presented with cancer presents to a health-care provider for examination. A sample having a cell, such as a biopsy specimen, is taken from the individual's body, whereupon the sample is contacted with an anti-nucleolin antibody, incubated, and the bound antibody then detected. The amount of bound antibody can be compared to the amount bound by healthy cells isolated from the same individual. A treatment regimen may then be devised, based on the quantity of cell-surface nucleolin per cell taken from the individual's body and a known correlation between cell-surface nucleolin and susceptibility of the cancer to a certain manner of therapy, such as chemotherapy targeting nucleolin.

Treatment of Tumor/Cancer Cells Targeting Nucleolin

In one embodiment, methods of treating cells in a neoplastic state including cancer and tumor cells, are provided; these methods exploit plasma membrane nucleolin which acts as a beacon for a therapeutic agent. For example, administration of anti-nucleolin antibodies, which may be conjugated to a toxin or other means of stimulating cell death or incurring necrosis, results in the removal of plasma membrane nucleolin-expressing cells.

Practicing the Invention

The following, not meant to limit the invention, is presented to aid the practitioner in carrying out the invention, although other methods, techniques, cells, reagents and approaches can be used to achieve the invention.

Cells

Cells or tissue samples are collected from a subject. The subject is a vertebrate, more preferably a mammal, such as a monkey, dog, cat, rabbit, cow, pig, goat, sheep, horse, rat, mouse, guinea pig, etc.; and most preferably a human. Any technique to collect the desired cells may be employed, including biopsy, surgery, scrape (inner cheek, skin, etc.) and blood withdrawal. Any appropriate tool may be used to carry out such tasks. It is not necessary to isolate the test population (i.e., those cells being tested for neoplastic state) from those cells and tissues (contaminating material) that are not being tested, except in some cases using biochemical methods that include extraction. In this last case, the test population need not be completely isolated from contaminating materials, but should either predominate or be easily distinguishable (e.g., morphologically (structurally, specific markers) or biochemically).

For those methods that analyze lung carcinomas, sputum collection is an attractive and easily obtained sample. The term "sputum" as used herein refers to expectorated matter made up of saliva and discharges from the respiratory airways. Sputum is a highly complex material that has a pronounced gel-like structure.

For collection of sputum, Byrne, et al., (Byrne, 1986) suggest that the patient collect material, raised by several deep coughs, in a container with a lid. Alternatively, sputum can be collected by using a bronchoscope (Kim et al., 1982). Specific devices or agents may be used to facilitate sputum collection (Babkes et al., 2001; King and Speert, 2002; Rubin and Newhouse, 1999). Other methods of sputum collection are also available.

Cell Culture

In some cases, culturing the harvested cells is desirable to augment their numbers so that plasma membrane nucleolin detection is facilitated. Suitable media and conditions for generating primary cultures are well known. The selection of the media and culture conditions vary depending on cell type and may be empirically determined. For example, skeletal muscle, bone, neurons, skin, liver, and embryonic stem cells are grown in media that differs in their specific contents. Furthermore, media for one cell type may differ significantly from laboratory to laboratory and institution to institution. To keep cells dividing, serum, such as fetal calf serum (FCS) (also known as fetal bovine serum (FBS)), is added to the medium in relatively large quantities, 5%-30% by volume, depending on cell or tissue type. Other sera include newborn calf serum (NCS), bovine calf serum (BCS), adult bovine serum (ABS), horse serum (HS), human, chicken, goat, porcine, rabbit and sheep sera. Serum replacements may also be used, such as controlled process serum replacement-type (CPSR; 1 or 3) or bovine embryonic fluid. Specific purified growth factors or cocktails of multiple growth factors can also be added or sometimes substituted for serum. Specific factors or hormones that promote proliferation or cell survival can also be used.

Examples of suitable culture media include Iscove's Modified Dulbecco's Medium (IMDM), Dulbecco's Modified Eagle's Medium (DMEM), Minimal Essential Medium Eagle (MEM), Basal Medium Eagle (BME), Click's Medium, L-15 Medium Leibovitz, McCoy's 5A Medium, Glasgow Minimum Essential Medium (GMEM), NCTC 109 Medium, Williams' Medium E, RPMI-1640, and Medium 199. A medium specifically developed for a particular cell type/line or cell function, e.g. Madin-Darby Bovine Kidney Growth Medium, Madin-Darby Bovine Kidney Maintenance Medium, various hybridoma media, Endothelial Basal Medium, Fibroblast Basal Medium, Keratinocyte Basal Medium, and Melanocyte Basal Medium are also known. If desired, a protein-reduced or -free and/or serum-free medium and/or chemically defined, animal component-free medium may be used, e.g., CHO, Gene Therapy Medium or QBSF Serum-free Medium (Sigma Chemical Co.; St. Louis, Mo.), DMEM Nutrient Mixture F-12 Ham, MCDB (105, 110, 131, 151, 153, 201 and 302), NCTC 135, Ultra DOMA PF or HL-1 (both from Biowhittaker; Walkersville, Md.), may be used.

The medium can be supplemented with a variety of growth factors, cytokines, serum, etc., depending on the cells being cultured. Examples of suitable growth factors include: basic fibroblast growth factor (bFGF), vascular endothelial growth factor (VEGF), epidermal growth factor (EGF), transforming growth factors (TGFα and TGFβ), platelet derived growth factors (PDGFs), hepatocyte growth factor (HGF), insulin-like growth factor (IGF), insulin, erythropoietin (EPO), and colony stimulating factor (CSF). Examples of suitable hormone additives are estrogen, progesterone, testosterone or glucocorticoids such as dexamethasone. Examples of cytokine medium additives are interferons, interleukins or tumor necrosis factor-α (TNFα). Salt solutions may also be added to the media, including Alseverr's Solution, Dulbecco's Phosphate Buffered Saline (DPBS), Earle's Balanced Salt Solution, Gey's Balanced Salt Solution (GBSS), Hanks' Balanced Salt Solution (HBSS), Puck's Saline A, and Tyrode's Salt Solution. If necessary, additives and culture components in different culture conditions be can optimized, as these may alter cell response, activity lifetime or other features affecting bioactivity. In addition, the surface on which the cells are grown can be coated with a variety of substrates that contribute to survival, growth and/or differentiation of the cells. These substrates include but are not limited to, laminin, EHS-matrix, collagens, poly-L-lysine, poly-D-lysine, polyornithine and fibronectin. When three-dimensional cultures are desired, extracellular matrix gels may be used, such as collagen, EHS-matrix, or gelatin (denatured collagen). Cells may be grown on top of such matrices, or may be cast within the gels themselves.

If desired, the media may be further supplemented with reagents that limit acidosis of the cultures, such as buffer addition to the medium (such as N,N-bis(2-hydroxyethyl)-2-aminoethanesulfonic acid (BES), bis(2-hydroxyethyl)amino-tris(hydroxymethyl)methane (BIS-Tris), N-(20hydroxyethyl)piperazine-N'3-propanesulfonic acid (EPPS or HEPPS), glyclclycine, N-2-hydroxyethylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminomethane (Tris), etc.). Frequent medium changes and changes in the supplied $CO_2$ (often approximately 5%) concentration may also be used to control acidosis.

Gases for culture typically are about 5% carbon dioxide and the remainder nitrogen, but optionally may contain varying mounts of nitric oxide (starting as low as 3 ppm), carbon monoxide and other gases, both inert and biologically active. Carbon dioxide concentrations typically range around 5%, but may vary between 2-10%. Both nitric oxide and carbon monoxide, when necessary, are typically administered in very small amounts (i.e. in the ppm range), determined empirically or from the literature. The temperature at which the cells will grow optimally can be empirically determined, although the culture temperature will usually be within the normal physiological range of the animal from which the cells were isolated.

Detecting Nucleolin: Antibody-Based Methods

Antibodies

Nucleolin can be detected at the protein level in cells, tissue sections, cultured cells and extracts thereof. Immunochemical methods to detect protein expression are well known and include, but are not limited to, Western blotting, immunoaffinity purification, immunoprecipitation, enzyme-linked immunosorbent assay (ELISA), dot or slot blotting, radioimmunoassay (RIA), immunohistochemical detection, immunocytochemical staining, and flow cytometry. Common procedures and instructions using antibodies have been well addressed (e.g., (Harlow and Lane, 1988; Harlow and Lane, 1999). Selected antibodies that are useful for detecting plasma membrane nucleolin are shown in Table 1.

TABLE 1

Anti-nucleolin antibodies

| Antibody | Source | Antigen source | Notes |
|---|---|---|---|
| p7-1A4 mouse monoclonal antibody (mAb) | Developmental Studies Hybridoma Bank (University of Iowa; Ames, IA) | *Xenopus laevis* oocytes | $IgG_1$ |
| sc-8031 mouse mAb | Santa Cruz Biotech (Santa Cruz, CA) | human | $IgG_1$ |
| sc-9893 goat polyclonal Ab (pAb) | Santa Cruz Biotech | human | IgG |
| sc-9892 goat pAb | Santa Cruz Biotech | human | IgG |
| clone 4E2 mouse mAb | MBL International (Watertown, MA) | human | $IgG_1$ |
| clone 3G4B2 mouse mAb | Upstate Biotechnology (Lake Placid, NY) | dog (MDCK cells) | $IgG_{1k}$ |

If additional anti-plasma membrane nucleolin antibodies are desired, they can be produced using well-known methods (Harlow and Lane, 1988; Harlow and Lane, 1999). For example, polyclonal antibodies (pAbs) can be raised in a mammalian host by one or more injections of an immunogen, such as an extracellular domain of surface-expressed nucleolin, and, if desired, an adjuvant. Typically, the immunogen (and adjuvant) is injected in a mammal by a subcutaneous or intraperitoneal injection. The immunogen may include components such as polypeptides (isolated, non-isolated, or recombinantly produced), cells or cell fractions. Examples of adjuvants include Freund's complete, monophosphoryl Lipid A synthetic-trehalose dicorynomycolate, aluminum hydroxide (alum), heat shock proteins HSP 70 or HSP96 (WO01/917871A1), squalene emulsion containing monophosphoryl lipid A (LaPosta and Eldrige, 2001), $α_2$-macroglobulin and surface active substances, including oil emulsions, pleuronic polyols, polyanions and dinitrophenol. To improve the immune response, an immunogen may be conjugated to a polypeptide that is immunogenic in the host, such as keyhole limpet hemocyanin (KLH), serum albumin, bovine thyroglobulin, cholera toxin, labile enterotoxin, or soybean trypsin inhibitor. Alternatively, pAbs may be made in chickens, producing IgY molecules (Schade et. al., 1996).

Monoclonal antibodies (mAbs) may also be made by immunizing a host or lymphocytes from a host, harvesting the mAb-secreting (or potentially secreting) lymphocytes, fusing those lymphocytes to immortalized cells (e.g., myeloma cells), and selecting those cells that secrete the desired mAb (Goding, 1996; Kohler and Milstein, 1975). Other techniques may be used, such as EBV-hybridoma technique (Cole et al., 1985; Coligan, 1996). Techniques for the generation of chimeric antibodies by splicing genes encoding the variable domains of non-human antibodies to genes of the constant domains of human immunoglobulin result in "chimeric antibodies" that are substantially human at the amino acid level (Neuberger, Williams et al. 1984; Morrison, Johnson et al. 1984). If desired, the mAbs may be purified from the culture medium or ascites fluid by conventional procedures, such as protein A-sepharose, hydroxylapatite chromatography, gel electrophoresis, dialysis, ammonium sulfate precipitation or affinity chromatography (Harlow and Lane, 1988; Harlow and Lane, 1999). Additionally, human monoclonal antibodies can be generated by immunization of transgenic mice containing a third copy IgG human trans-loci and silenced endogenous mouse Ig loci (Surani et al., 1996) or using human-transgenic mice (Jakobovits et al., 1998; Lonberg and Kay, 1998). Production of humanized monclonal antibodies and fragments thereof can also be generated through phage display technologies (Winter, Griffiths et al. 1994).

An example of the production of a murine monoclonal antibody to human nucleolin according to described techniques (Kohler and Milstein, 1975) is as follows. Female BALB/c mice (20-25 g) are injected intraperitoneally with 100 μg of antigen containing human nucleolin polypeptide, or portion thereof. Alternatively, the antigen includes murine cells which have been transformed to express human nucleolin. After 2 weeks, a second injection having 50 μg of antigen is injected. To test for production of anti-nucleolin antibodies, sera from the mice are used in immunohistologic screening. Mice displaying high blood serum levels of anti-nucleolin antibody receive a third injection (20 μg) of antigen. Four days later, the mice are sacrificed, their spleen cells isolated and fused with a myeloma line, e.g., P3X63Ag8.653 (American Type Tissue Collection; Manassas, Va.). The resulting hybridoma cells are cultured, sub-cloned and selected for expression of antibodies having high affinities for nucleolin.

Non-immunogenic human-like or humanized polyclonal antibodies that bind to nucleolin may also be produced. These polyclonal antibodies can be made, for example, using phage display methods (Sharon, 1995), or by immunizing transgenic or genetically engineered animals capable of producing human polyclonal antibodies (Singh and Dias, 2002).

Antibodies Suitable for Therapy

Antibodies most ideal for use as therapeutics are those that are non-immunogenic when administered to subjects. Such antibodies have the advantages of exerting minimal side-effects, having long serum and biologic half-life, having wide bio-distribution, having high target specificity and high activity in engaging the effector phase of the immune system. These antibodies, when intended for human subjects, are commonly referred to as "humanized," "human," "chimeric," or "primatized" antibodies; these are comprised substantially (>70%) of human amino acid sequences.

Detection

An approach using antibodies to detect the presence of an antigen will include one or more, if not all, of the following steps:

(1) Preparing the entity being tested for plasma membrane nucleolin by washing with buffer or water
(2) Blocking non-specific antibody binding sites
(3) Applying the antibody (e.g., nucleolin)
(4) Detecting bound antibody, either via a detectable labeled-secondary antibody that recognizes the primary antibody or a detectable label that has been directly attached to, or associated with, the bound (anti-nucleolin) antibody.

Substrates may be washed with any solution that does not interfere with the epitope structure. Common buffers include saline and biological buffers, such as bicine, tricine, and Tris.

Non-specific binding sites are blocked by applying a protein solution, such as bovine serum albumin (BSA; denatured or native), milk proteins, or in the cases wherein the detecting reagent is a secondary antibody, normal serum or immunoglobulins from a non-immunized host animal whose species is the same origin as the detecting antibody. For example, a procedure using a secondary antibody made in goats would employ normal goat serum (NGS).

The substrate is then reacted with the antibody of interest. The antibody may be applied in any form, such as Fab fragments and derivatives thereof, purified antibody (by affinity, precipitation, etc.), supernatant from hybridoma cultures, ascites, serum or recombinant antibodies expressed in recombinant cells. The antibody may be diluted in buffer or media, often with a protein carrier such as the solution used to block non-specific binding sites; the useful antibody concentration is usually determined empirically. In general, polyclonal sera, purified antibodies and ascites may be diluted 1:50 to 1:200,000, more often, 1:200 to 1:500. Hybridoma supernatants may be diluted 1:0 to 1:10, or may be concentrated by dialysis or ammonium sulfate precipitation (or any other method that retains the antibodies of interest but at least partially removes the liquid component and preferably other small molecules, such as salts) and diluted if necessary. Incubation with antibodies may be carried out for as little as 20 minutes at 37° C., 2 to 6 hours at room temperature (approximately 22° C.), or 8 hours or more at 4° C.

To detect an antibody-antigen complex, a label may be used. The label may be coupled to the binding antibody, or to a second antibody that recognizes the first antibody, and is incubated with the sample after the primary antibody incubation and thorough washing. Suitable labels include fluorescent moieties, such as fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3 and 5; phycoerythrin; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives; pyrenes; pyridyloxazole derivatives; dapoxyl dyes; Cascade Blue and Yellow dyes; benzofuran isothiocyanates; sodium tetrafluorophenols; 4,4-difluoro-4-bora-3a,4a-diaza-s-indacene. Suitable labels further include enzymatic moieties, such as alkaline phosphatase or horseradish peroxidase; radioactive moieties, including $^{35}S$ and $^{135}I$-labels; avidin (or streptavidin)-biotin-based detection systems (often coupled with enzymatic or gold signal systems); and gold particles. In the case of enzymatic-based detection systems, the enzyme is reacted with an appropriate substrate, such as 3,3'-diaminobenzidine (DAB) for horseradish peroxidase; preferably, the reaction products are insoluble. Gold-labeled samples, if not prepared for ultra-structural analyses, may be chemically reacted to enhance the gold signal; this approach is especially desirable for light microscopy. The choice of the label depends on the application, the desired resolution and the desired observation methods. For fluorescent labels, the fluorophore is excited with the appropriate wavelength and the sample observed using a microscope, confocal microscope, or FACS machine. In the case of radioactive labeling, the samples are contacted with autoradiography film, and the film developed; alternatively, autoradiography may also be accomplished using ultrastructural approaches. Alternatively, radioactivity may be quantified using a scintillation counter.

The invention also provides methods for the detection of a tumor in an individual in vivo. The individual is administered a pharmaceutically acceptable composition having an agent that binds cell-surface nucleolin. The agent also incorporates a detectable label, such as a radiolabel, which distribution in the subject's body is then mapped. The agent may comprise an aptamer, an oligonucleotide, a peptide, a small molecule, or a macromolecule, such as an antibody.

In one example of the method, a composition that specifically binds to tumor cell surface nucleolin is radiolabeled. The nature of the radiolabel is determined by the device that is used to record the presence and distribution of the agent in the patient's body. For example, if standard radio-imaging using gamma cameras is used, any one of several radioisotopes is used, such as technetium-99 or indium-111. Alternatively, if positron emission tomography (PET) is used, then the radiolabel is a radioactive halogen, such as flourine-18. The patient is injected intravenously with the radiolabeled agent, and scans of the patient, to visualize the location of the agent, are performed over the following 12 hour period, at, for example, 1, 4, and 12 hours post-injection. Monitoring techniques include whole body scanning, SPECT (which allows cross-sections of the body to be visualized), and any technique that permits monitoring of emission.

Cytological-Based Approaches:

Immunofluorescence/Immunohistochemical

Protein expression by cells or tissue can be ascertained by immunolocalization of an antigen. Generally, cells or tissue are preserved by fixation, exposed to an antibody that recognizes the epitope of interest, such as a nucleolin, and the bound antibody visualized.

Any cell, cell line, tissue, or even an entire organism is appropriate for fixation. Cells may be cultured in vitro as primary cultures, cell lines, or harvested from tissue and separated mechanically or enzymatically. Tissue may be from any organ, plant or animal, and may be harvested after or prior to fixation. Fixation, if desired, may be by any known means; the requirements are that the protein to be detected be not rendered unrecognizable by the binding agent, most often an antibody. Appropriate fixatives include paraformaldehyde-lysine-periodate, formalin, paraformaldehyde, methanol, acetic acid-methanol, glutaraldehyde, acetone, Karnovsky's fixative, etc. The choice of fixative depends on variables such as the protein of interest, the properties of a particular detecting reagent (such as an antibody), the method of detection (fluorescence, enzymatic) and the method of observation (epifluorescence microscopy, confocal microscopy, light microscopy, electron microscopy, etc.). The sample is usually first washed, most often with a biological buffer, prior to fixation. Fixatives are prepared in solution or in biological buffers; many fixatives are prepared immediately prior to applying to the sample. Suitable biological buffers include saline (e.g., phosphate buffered saline), N-(carbamoylmethyl)-2-aminoethanesulfonic acid (ACES), N-2-acetamido-2-iminodiacetic acid (ADA), bicine, bis-tris, 3-cyclohexylamino-2-hydroxy-1-propanesulfonic acid (CAPSO), ethanolamines, glycine, N-2-hydroxyethylpiperazine-N'-2-ethanesulfonic acid (HEPES), 2-N-morpholinoethanesulfonic acid (MES), 3-N-morpholinopropanesulfonic acid (MOPS), 3-N-morpholino-2-hyrdoxy-propanesulfonic acid (MOPSO), piperazine-N,N'-bis(2-ethanesulfonic acid) (PIPES), tricine, triethanolamine, etc. An appropriate buffer is selected according to the sample being analyzed, appropriate pH, and the requirements of the detection method. A useful buffer is phosphate buffered saline (PBS). After fixation, the sample may be stored in fixative, preferably fresh, or temporarily or indefinitely, at a temperature between about 4° C. to about 22° C.

After fixation from 5 minutes to 1 week, depending on the sample size, sample thickness, and viscosity of the fixative, the sample is washed in buffer. If the sample is thick or sections are desired, the sample may be embedded in a suitable matrix. For cryosectioning, sucrose is infused, and embedded in a matrix, such as OCT Tissue Tek (Andwin Scientific; Canoga Park, Calif.) or gelatin. Samples may also be embedded in paraffin wax, or resins suitable for electron microscopy, such as epoxy-based (Araldite, Polybed 812, Durcupan ACM, Quetol, Spurr's, or mixtures thereof; Polysciences, Warrington, Pa.), acrylates (London Resins (LR White, LR gold), Lowicryls, Unicryl; Polysciences), methylacrylates (JB-4, OsteoBed; Polysciences), melamine (Nanoplast; Polysciences) and other media, such as DGD, Immuno-Bed (Polysciences) and then polymerized. Resins that are especially appropriate include hydrophilic (such as Lowicryls, London Resins, water-soluble Durcupan, etc.) since these are less likely to denature the protein of interest during polymerization and will not repel antibody solutions. When embedded in wax or resin, samples are dehydrated by passing them through a concentration series of ethanol or methanol; in some cases, other solvents may be used, such as polypropylene oxide. Embedding may occur after the sample has been reacted with the detecting agents, or samples may be first embedded, sectioned (via microtome, cyrotome, or ultramicrotome), and then the sections reacted with the detecting reagents. In some cases, the embedding material may be partially or completely removed before detection to facilitate antigen access.

In some instances, the nucleolin epitope(s) to which the antibody binds may be rendered unavailable because of fixation. Antigen retrieval methods can be used to make the antigen available for antibody binding. Many recourses are available (reviewed in, for example, (McNicol and Richmond, 1998; Robinson and Vandre, 2001; Shi et al., 2001)). Common methods include using heat supplied from autoclaves, microwaves, hot water or buffers, pressure cookers, or other sources of heat. Often the sources of heat are used in sequence; the samples must often be in solution (e.g., microwave treatments). Detergent treatment may also unmask antigens, such as sodium dodecyl sulfate (SDS, 0.25% to 1%) or other denaturing detergents. Chemical methods include strong alkalis (such as NaOH), prolonged immersion in water, urea, formic acid and refixation in zinc sulfate-formalin. In other instances, proteolytic enzyme treatment will modify the antigen such that it is available to the antibody. Any number of proteases may be used, such as trypsin. These methods may be combined to achieve optimal results. The choice of the antigen retrieval method will depend on the sample, its embedment (if any), and the anti-nucleolin antibody.

Especially in the cases of immunofluorescent or enzymatic product-based detection, background signal due to residual fixative, protein cross-linking, protein precipitation or endogenous enzymes may be quenched, using, e.g., ammonium chloride or sodium borohydride or a substance to deactivate or deplete confounding endogenous enzymes, such as hydrogen peroxide which acts on peroxidases. To detect intracellular proteins in samples that are not to be sectioned, samples may be permeabilized. Permeabilizing agents include detergents, such as t-octylphenoxypolyethoxyethanols, polyoxyethylenesorbitans, and other agents, such as lysins, proteases, etc.

Non-specific binding sites are blocked by applying a protein solution, such as bovine serum albumin (BSA; denatured or native), milk proteins, or preferably in the cases wherein the detecting reagent is an antibody, normal serum or IgG from a non-immunized host animal whose species is the same is the same origin of the detecting antibody.

Flow Cytometry/Fluorescence-Activated Cell Sorting (FACS)

Methods of performing flow cytometry are well known (Orfao and Ruiz-Arguelles, 1996). Because plasma membrane nucleolin is being probed, cell permeabilization that allows access to cytoplasmic compartments is undesirable. After harvesting, cells are prepared as a single-cell suspension; cells are then incubated with an anti-nucleolin antibody usually after blocking non-specific binding sites. Preferably, the anti-nucleolin antibody is labeled with a fluorescent marker. If the antibody is not labeled with a fluorescent marker, a second antibody that is immunoreactive with the first antibody and contains a fluorescent marker is used. After sufficient washing to ensure that excess or unbound antibodies are removed, the cells are ready for flow cytometry.

Biochemical-Based Approaches:

In these approaches, it is first desirable to isolate plasma membrane proteins from other cellular compartments. This may be done in any number of ways, such as simple cell extraction, differential extraction or mechanical disruption followed by separation of cellular compartments on gradients (such as sucrose or polydextran) by centrifugation, extraction followed by immunoselecting appropriate cellular compartments with plasma membrane-specific antibodies, etc. An example of such an approach is described in (Naito et al., 1988; Yao et al., 1996b)). Extracting reagents are well known. For examples, solvents such as methanol may be occasionally useful. More likely, detergents, such as t-octylphenoxypolyethoxyethanol (also known as polyethylene glycol tert-octylphenyl ether) are particularly useful for simple extractions. Also useful are glucopyranosides, maltopyranosides, maltosides, polyoxyethylene esters, other polyoxyethylene ethers, salts of alginic, caprylic, cholic 1-decanesulfonic, deoxycholic, dioctyl sulfosuccinate, 1-dodecanesulfonic, glyocholic, glycodeoxycholic, 1-heptanesulfonic, 1-hexanesulfonic, N-lauroylsacrosine, lauryl sulfate (e.g., SDS), 1-nonanesulfonic, 1-octanesulfonic, 1-pentanesulfonic, taurocholic and tauodexycholic acids; sodium 7-ethyl-2-methyl-4-undecyl sulfate, and sodium 2-ethylhexyl sulfate. Other useful detergents include (3-[(3-cholamidopropyl)dimethylammonio]-1-propane-sulfonate, (3-[(3-cholamidopropyl)dimethylammonio]-2-hydroxy-1-propane-sulfonate, N-decyl-, N-dodecyl-, N-hexadecyl-, N-octadecyl-, N-tetradecyl-N,N-dimethyl-3-ammonio-1-propanesulfonates and phosphatidylcholine. Less useful, but may be helpful in some cases, are alkyltrimethylammonium bromides, benzalkonium chloride, benzethonium chloride, benzyldimethyldodecylammonium bromide, benzyldimethylhexadecylammonium chloride, cetyldimethylethylammonium bromide, cetylpyridinium, decamethonium bormide, dimethyldioctadecylammonium bromide, methylbenzethonium chloride, methyltiroctylammonium chloride, and N,N',N'-polyoxyehtlylene(10)-N-tallow-1,3-diaminopropane. The different extracting reagents may be used singly or in combination; they may be prepared in simple aqueous solutions or suitable buffers.

Polyethylene glycol ter-octylphenyl ether is particularly useful for differential extraction by taking advantage of the low cloud point to separate membrane proteins from soluble proteins into two different phases.

Extraction buffers may contain protease inhibitors, such as aprotinin, benzamidine, antipain, pepstatin and iodoacetamide.

Extracts are then assayed for nucleolin expression. For those techniques that separate surface plasma membrane from other cellular components (especially the nucleus), the nucleolin detecting agents need not be specific for extracellular plasma membrane nucleolin epitopes.

Immunosorbent Assay (ELISA) (Ausubel et al. 1987)

Various types of enzyme linked immunosorbent assays (ELISAs) to detect protein expression are known, and these are applicable to nucleolin detection. However, other ELISA-like assays include radio-immunoassays and other non-enzyme linked antibody binding assays and procedures. In these assays, the cell surface proteins are the principle components in the cell preparation.

The double antibody-sandwich ELISA technique is especially useful. The basic protocol for a double antibody-sandwich ELISA is as follows: A plate is coated with anti-nucleolin antibodies (capture antibodies). The plate is then washed with a blocking agent, such as BSA, to block non-specific binding of proteins (antibodies or antigens) to the test plate. The test sample is then incubated on the plate coated with the capture antibodies. The plate is then washed, incubated with anti-nucleolin antibodies, washed again, and incubated with a specific antibody-labeled conjugates and the signal appropriately detected.

In other ELISAs, proteins or peptides are immobilized onto a selected surface, the surface exhibit may have affinity for proteins, such as the wells of a specially-treated polystyrene microtiter plate. After washing to remove incompletely adsorbed material, one would then generally desire to bind or coat with a nonspecific protein that is known to be antigenically neutral with anti-nucleolin antibodies, such as BSA or casein, onto the well bottom. This step allows for blocking of nonspecific adsorption sites on the immobilizing surface and thus reduces the background caused by nonspecific binding of antibodies onto the surface. When the antibodies were created in an animal by conjugating a polypeptide to a protein (e.g., BSA), a different protein is usually used as a blocking agent, because of the possibility of the presence of antibodies to the blocking protein the antibody composition.

After binding of nucleolin to the well, coating with a non-reactive material to reduce background, and washing to remove unbound material, the immobilizing surface is contacted with an anti-nucleolin antibody composition in a manner conducive to immune complex (antigen/antibody) formation. Such conditions include diluting the antibody composition with diluents such as BSA, bovine γ globulin (BGG) and PBS/Polyoxyethylenesorbitan monolaurate. These added agents also assist in the reduction of nonspecific background signal. The layered antibody composition is then allowed to incubate for, e.g., from 2 to 4 hours at 25° C. to 37° C. Following incubation, the antibody composition-contacted surface is washed so as to remove non-immunocomplexed material. One washing procedure includes washing with a PBS/polyoxyethylenesorbitan monolaurate or borate buffer solution.

Following formation of specific immunocomplexes between the test sample and the antibody and subsequent washing, immunocomplex formation is detected using a second antibody having specificity for the anti-nucleolin antibody. For detection, the secondary antibody is associated with detectable label, such as an enzyme or a fluorescent molecule. A number of immunoassays are discussed in U.S. Pat. Nos. 5,736,348, 5,192,660, and 4,474,892.

Western Blotting (Ausubel et al., 1987)

Western blotting methods are well known. Generally, a protein sample is subjected to sodium dodecyl sulfate-polyacrylamide gel electrophoresis (SDS-PAGE) at such conditions as to yield an appropriate separation of proteins within the sample. The proteins are then transferred to a membrane (e.g., nitrocellulose, nylon, etc.) in such a way as to maintain the relative positions of the proteins to each other.

Visibly labeled proteins of known molecular weight may be included within a lane of the gel. These proteins serve as a control to insure adequate transfer of the proteins to the membrane, as well as molecular weight markers for determining the relative molecular weight of other proteins on the blot. Alternatively, unlabeled marker proteins (or in some rare instances, no marker proteins) are detected after transfer with Brilliant Blue (G or R; Sigma; St. Louis, Mo.) other protein dyes. After protein transfer, the membrane is submersed in a blocking solution to prevent nonspecific binding of the primary antibody.

The primary antibody, e.g., anti-nucleolin, may be labeled and the presence and molecular weight of the antigen may be determined by detecting the label at a specific location on the membrane. However, the primary antibody may not be labeled, and the blot is further reacted with a labeled second antibody. This secondary antibody is immunoreactive with the primary antibody; for example, the secondary antibody may be one to rabbit immunoglobulins and labeled with alkaline phosphatase. An apparatus for and methods of performing Western blots are described in U.S. Pat. No. 5,567,595.

Immunoprecipitation (Ausubel et al., 1987; Harlow and Lane, 1999)

Protein expression can be determined and quantified by isolating antigens using immunoprecipitation. Methods of immunoprecipitations are described in U.S. Pat. No. 5,629,197. Immunoprecipitation involves the separation of the target antigen component from a complex mixture and is used to discriminate or isolate minute amounts of protein. For the isolation of cell-surface proteins, nonionic salts are often used.

For example, an immunoprecipitation from whole cells may be performed as follows. Cells are extracted with one or more detergents (see above), such as, for example, 1% t-octylphenoxypolyethoxyethanol/0.1% SDS/150 mM NaCl in 20 mM Tris buffer, pH 8.6. After extraction, which may be aided by agitation, insoluble debris is removed using a centrifuge. Anti-nucleolin antibody is added to the extracts, and then the samples are incubated 30 minutes to overnight at 4° C. *Staphylococcus aureus* or recombinantly-produced Protein A or Group C *Staphylococcus* Protein G conjugated to sepharose or tris-acryl beads are then added. In those instances when the anti-nucleolin antibody does not bind well to Protein A, IgG Abs that recognize antibodies of the animal in which the anti-nucleolin antibody was made is simultaneously added. The samples are then incubated with gentle agitation for around 2 hours at 4° C. The beads or bacterial cells, now bound to the antibody-antigen complexes, are thoroughly washed, usually first with either the extraction solution or a high salt buffer, then a salt-less buffer or water to remove nonspecifically-bound proteins and residual detergent molecules. After removing residual buffer, the beads are incubated with a buffer, such as electrophoresis sample buffer, and then subjected to 95° C. for 3-5 minutes to elute bound proteins from the beads. The samples are then ready for analysis and nucleolin detection.

Other Methods:

Immunoselection Procedures (Other than FACS) (Ausubel et al., 1987)

Cells expressing plasma membrane nucleolin can be easily isolated by "panning" on plastic plates coated with anti-antibody antibodies (Wysocki and Sato, 1978). Panning has many advantages over other immunoselection procedures: It is fast, efficient ($10^7$ cells can easily be panned on two 60-mm plastic plates in 30 minutes), and inexpensive.

In general, a single cell suspension is labeled with an anti-nucleolin antibody, and then is incubated on a substrate coated with a secondary antibody (with non-specific binding sites blocked). After 1 to 3 hours incubation at room temperature, non-adherent cells are washed away. In this embodiment, bound cells indicate that nucleolin is expressed in the plasma membrane, indicating a neoplastic cell.

Detecting Nucleolin: Oligonucleotide-Based Methods

GROs and other oligonucleotides that recognize and bind nucleolin (Bates et al., 1999; Miller et al., 2000; Xu et al., 2001) can be used much the same way as antibodies are. Examples of suitable assays are given below. In some cases, incorporating the GRO nucleotides into larger nucleic acid sequences may be advantageous; for example, to facilitate binding of a GRO nucleic acid to a substrate without denaturing the nucleolin-binding site.

Useful GROs that bind nucleolin (and also have the biological property of inhibiting cancer cell growth) have been described (Bates et al., 1999; Miller et al., 2000; Xu et al., 2001). They include those shown in Table 2. Control GROs are useful for detecting background signal levels.

TABLE 2

Non-anti-sense GRO that bind nucleolin and non-binding controls[1, 2, 3]

| GRO | Sequence | SEQ ID NO: |
|---|---|---|
| GRO29A[1] | tttggtggtg gtggttgtgq tggtggtgg | 1 |
| GRO29-2 | tttggtggtg gtggttttgg tggtggtgg | 2 |
| GRO29-3 | tttggtggtg gtqgtggtgg tggtggtgg | 3 |
| GRO29-5 | tttggtggtg gtggtttggg tggtggtgg | 4 |
| GRO29-13 | tggtggtggt ggt | 5 |
| GRO14C | ggtggttgtg gtgg | 6 |

TABLE 2-continued

Non-anti-sense GRO that bind nucleolin and non-binding controls[1, 2, 3]

| GRO | Sequence | SEQ ID NO: |
|---|---|---|
| GRO15A | gttgtttggg gtggt | 7 |
| GRO15B[2] | ttggggggggg tgggt | 8 |
| GRO25A | ggttggggtg ggtggggtgg gtggg | 9 |
| GRO26B[1] | ggtggtggtg gttgtggtgg tggtgg | 10 |
| GRO28A | tttggtggtg gtggttgtgg tggtggtg | 11 |
| GRO28B | tttggtggtg gtggtgtggt ggtggtgg | 12 |
| GRO29-6 | ggtggtggtg gttgtggtgg tggtggttt | 13 |
| GRO32A | ggtggttgtg gtggttgtgg tggttgtggt gg | 14 |
| GRO32B | tttggtggtg gtggttgtgg tggtggtggt tt | 15 |
| GRO56A | ggtggtggtg gttgtggtgg tggtggttgt ggtggtggtg gttgtggtgg tggtgg | 16 |
| CRO | tttcctcctc ctccttctcc tcctcctcc | 18 |
| GRO A | ttagggttag ggttagggtt aggg | 19 |
| GRO B | ggtggtggtg g | 20 |
| GRO C | ggtggttgtg gtgg | 21 |
| GRO D | ggtggtgtg gttgg | 22 |
| GRO E | gggttttggg | 23 |
| GRO F | ggttttggtt ttggttttgg | 24 |
| GRO G[1] | ggtggtgtg gttgg | 25 |
| GRO H[1] | ggggttttgg gg | 26 |
| GRO I[1] | gggttttggg | 27 |
| GRO J[1] | ggggttttgg ggttttgggg ttttgggg | 28 |
| GRO K[1] | ttggggttgg ggttggggtt gggg | 29 |
| GRO L[1] | gggtgggtgg gtgggt | 30 |
| GRO M[1] | ggttttggtt ttggttttgg ttttgg | 31 |
| GRO N[2] | tttcctcctc ctccttctcc tcctcctcc | 32 |
| GRO O[2] | cctcctcctc cttctcctcc tcctcc | 33 |
| GRO P[2] | tggggt | 34 |
| GRO Q[2] | gcatgct | 35 |
| GRO R[2] | gcggtttgcg g | 36 |
| GRO S[2] | tagg | 37 |
| GRO T[2] | ggggttgggg tgtggggttg ggg | 38 |

[1]Indicates a good plasma membrane nucleolin-binding GRO.
[2]Indicates a nucleolin control (non-plasma membrane nucleolin binding).
[3]GRO sequence without [1] or [2] designations have some anti-proliferative activity.

Cytological-Based Approaches:
Cellular Localization/Labeling (Relative of Immuno-Based Localization/Labeling Assays)

The procedures outlined above for the immuno-based localization assays (such as immunofluorescence or FACS) are also applicable to those assays wherein the detecting reagent is a nucleolin-binding GRO. Modifications include those to prevent non-specific binding, using denatured DNA, such as from salmon sperm instead of a protein such as BSA. For detection, similar labels as outlined above are also useful as long as the GRO can be derivatized with the label in some form. For this purpose, biotin-avidin nucleic acid labeling systems are especially convenient, as are digoxigenin ones (Ausubel et al., 1987). The synthesis of biotinylated nucleotides has been described (Langer et al., 1981). Biotin, a water-soluble vitamin, can covalently attached to the C5 position of the pyrimidine ring via an alylamine linker arm; biotin non-covalently binds avidin or streptavidin, which may be easily labeled. Alternatively, biotin is added to oligonucleotides during synthesis by coupling to the 5'-hydroxyl of the terminal nucleotide. Digoxigenin-11-dUTP can be incorporated into DNA by either nick translation or random oligonucleotide-primed synthesis protocols. Digoxigenin is detected using labeled anti-digoxigenin antibodies. Convenient digoxigenin systems are commercially available (Roche Molecular Biochemicals; Indianapolis, Ind.). An example of a procedure using oligonucleotides to detect and localize proteins has been described by (Davis et al., 1998).

Biochemical-Based Approaches:

GROs may also be used in a similar fashion as antibodies to detect nucleolin in biochemical approaches, as described above. For example, "Southwestern"-type blotting experiments may be performed with GROs (Bates et al., 1999; Miller et al., 2000). After cells have been appropriately extracted (for example, differentially to separate plasma membrane proteins from intracellular proteins), the proteins are subjected to electrophoresis on polyacrylamide gels and transferred to a substrate, such as a polyvinliden difluoride membrane. Proteins are denatured and renatured by washing for 30 minutes at 4° C. with 6 M gaunidine-HCl, followed by washes in 3 M, 1.5 M and 0.75 M guanidine HCl in 25 mM HEPES (pH 7.9)/4 mM KCl/3 mM $MgCl_2$). After blocking non-specific binding sites with 5% non-fat dried milk in HEPES buffer, the labeled GRO is hybridized for 2 hours at 4° C. in HEPES binding buffer supplemented with 0.25% NDM, 0.05% NP-40, 400 ng/ml salmon sperm DNA and 100 ng/ml of an unrelated mixed sequence oligonucleotide, such as tcgagaaaaa ctctcctctc cttccttcct ctcca; SEQ ID NO:17. After washing with HEPES binding buffer, the signal is detected appropriately.

Other Methods:

Arrays

Arrays of Immobilized Nucleolin-Binding Reagents on Chips

A chip is an array of regions containing immobilized molecules, separated by regions containing no molecules or immobilized molecules at a much lower density. For example, a protein chip may be prepared by applying nucleolin-binding antibodies; an "aptamer"-like chip may be prepared by applying nucleolin binding GROs. The remaining regions are left uncovered or are covered with inert molecules. The arrays can be rinsed to remove all but the specifically immobilized polypeptides or nucleic acids. In addition, chips may also be prepared containing multiple nucleolin-binding antibodies (Table 1), nucleic acids (such as GROs; Table 2), or both, and may contain control antibodies and/or nucleic acids that are non-reactive with nucleolin. Such an array would allow for simultaneous test confirmation, duplication and internal controls.

Proteins, such as anti-nucleolin antibodies, can be immobilized onto solid supports by simple chemical reactions, including the condensation of amines with carboxylic acids and the formation of disulfides. This covalent immobilization of proteins on inert substrates can prevent high background signals due to non-specific adsorption. Substrates derivatized with other molecules, such as biotin, are also useful when the protein to be immobilized is derivatized with avidin or streptavidin, or vice-versa. In some rare cases, especially when anti-nucleolin antibody-encoding nucleic acid sequences are available, fusion polypeptides comprising anti-nucleolin antibody may be advantageous for immobilization onto a substrate.

The surface may be any material to which a the nucleolin binding agent can be immobilized. For example, the surface may be metal, glass, ceramic, polymer, wood or biological tissue. The surface may include a substrate of a given material and a layer or layers of another material on a portion or the entire surface of the substrate. The surfaces may be any of the common surfaces used for affinity chromatography, such as those used for immobilization of glutathione for the purification of GST fusion polypeptides. The surfaces for affinity chromatography include, for example, sepharose, agarose, polyacrylamide, polystyrene and dextran. The surface need not be a solid, but may be a colloid, an exfoliated mineral clay, a lipid monolayer, a lipid bilayer, a gel, or a porous material.

The immobilization method desirably controls the position of the nucleolin binding agent on the surface; for example, enabling the antigen binding portions of antibodies unattached to the substrate, while the non-antigen binding portions are rooted to the substrate. By controlling the position of individual reactant ligands, patterns or arrays of the ligands may be produced. The portions of the surface that are not occupied by the nucleolin-binding reagent do not allow non-specific adsorption of polypeptides or polynucleotides.

In this embodiment, a sample from a subject, for example, blood, is passed over a chip containing nucleolin-binding molecules. A biosensing device, such as machine that detects changes in surface plasmon resonance, is then used to detect bound nucleolin. BIAcore (Uppsala, Sweden) chips serve as examples of useful chips and detection machines.

Prognostic Assays

Diagnostic methods can furthermore be used to identify subjects having, or at risk of developing, a neoplasia at an early stage of disease development, since the surface expression of nucleolin can be detected earlier than in conventional methods. Prognostic assays can be used to identify a subject having or at risk for developing a neoplasia, such as a subject who has a family history of harmful neoplasias, especially cancers. A method for identifying such an individual would include a test sample obtained from a subject and testing for cell surface localization of nucleolin.

In another embodiment, detecting plasma membrane nucleolin and then either qualitatively or quantitatively assessing the amount of nucleolin (usually indirectly through the signal generated from bound nucleolin molecules) can indicate the rate of cell proliferation, since plasma membrane nucleolin levels correlate with cell proliferation rates.

Kits

Kits, containers, packs, or dispensers containing nucleolin probes and detection reagents, together with instructions for administration, may be assembled. When supplied as a kit, the different components may be packaged in separate containers and admixed immediately before use. Such packaging of the components separately may permit long-term storage without losing the active components' functions.

Kits may also include reagents in separate containers that facilitate the execution of a specific test, such as diagnostic tests. For example, non-nucleolin-binding GROs may be supplied for internal negative controls, or nucleolin and a nucleolin-binding reagent for internal positive controls. The components of a kit are an anti-nucleolin agent used to probe for nucleolin, a control sample, and optionally a composition to detect nucleolin. Examples of anti-nucleolin agents include an anti-nucleolin antibody (e.g., as shown in Table 1) or fragment thereof; if labeled, then a nucleolin-binding detection reagent is superfluous. A nucleolin-binding oligonucleotide (e.g., as shown in Table 2), which may be derivatized such that a second labeled reagent may bind (such as biotin). However, if a labeled GRO nucleic acid is provided, then a second labeled reagent is superfluous. Examples of detection reagents include: labeled secondary antibodies, for example, an anti-mouse pAb made in donkey and then tagged with a fluorophore such as rhodamine, or a labeled reagent to detect oligonucleotides such as GROs; for example, avidin or streptavidin linked to horseradish peroxidase when the probe is biotinylated. Control components may include: normal serum from the animal in which a secondary antibody was made; a solution containing nucleolin polypeptide or nucleolin binding oligonucleotide; a dot blot of nucleolin protein to assay nucleolin-binding reagent reactivity; or fixed or preserved cells that express nucleolin in the plasma membrane. Other components may include buffers, fixatives, blocking solutions, microscope slides and/or cover slips or other suitable substrates for analysis, such as microtiter plates; detergent or detergent solutions or other cell extraction reagents; miscellaneous reagents, protease inhibitors, various containers and miscellaneous tools and equipment to facilitate the assays.

(a) Containers or Vessels

The reagents included in the kits can be supplied in containers of any sort such that the life of the different components are preserved and are not adsorbed or altered by the materials of the container. For example, sealed glass ampules may contain lyophilized nucleolin binding reagents (such as anti-nucleolin antibodies or nucleolin-binding oligonucleotides) or buffers that have been packaged under a neutral, non-reacting gas, such as nitrogen. Ampules may consist of any suitable material, such as glass, organic polymers (i.e., polycarbonate, polystyrene, etc.), ceramic, metal or any other material typically employed to hold reagents. Other examples of suitable containers include simple bottles that may be fabricated from similar substances as ampules, and envelopes that may have foil-lined interiors, such as aluminum or alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

(b) Instructional Materials

Kits may also be supplied with instructional materials. Instructions may be printed on paper or other substrate and/or may be supplied as an electronic-readable medium, such as a floppy disc, CD-ROM, DVD-ROM, DVD, videotape, audio tape, etc. Detailed instructions may not be physically associated with the kit; instead, a user may be directed to an internet web site specified by the manufacturer or distributor of the kit, or supplied as electronic mail.

Methods of Treatment

Therapeutic Methods

Another aspect of the invention pertains to methods of modulating nucleolin expression or activity for therapeutic purposes. The modulatory method of the invention involves contacting a cell with an agent that modulates one or more of the activities of nucleolin activity associated with the cell. An agent that modulates nucleolin activity can be a nucleic acid or a protein, a naturally occurring cognate ligand of nucleolin, a peptide, a nucleolin peptidomimetic, or other small molecule. Modulatory methods can be performed in vivo (e.g., by administering the agent to a subject). As such, the invention provides methods of treating an individual afflicted with a disease or disorder characterized by aberrant expression or activity of a nucleolin.

Anti-Nucleolin Antibodies as Therapeutic Agents

Any antibody, as described in "Detecting nucleolin: antibody-based methods: Antibodies," above, that binds and interferes with nucleolin may be used to treat tumors and cancers. In certain instances, monoclonal antibodies are preferred as they bind single, specific and defined epitopes. In other instances, however, polyclonal antibodies capable of interacting with more than one epitope on nucleolin are preferred. The antibodies may be whole antibodies and fragments or derivatives thereof. For example, when assaying live cells, using Fab fragments will eliminate cross-linking, thus preventing cells from endocytosing bound antibodies.

Spliceosome-Mediated RNA Trans-Splicing (SMaRT) (Mitchell, 1997)

In another embodiment, a subset of cells expressing select members of nucleolin is targeted through spliceosome-mediated RNA trans-splicing. This method is a means for expressing a heterologous gene in a selected subset of cells by targeting a trans-splicing reaction between a precursor therapeutic molecule (PMT) and pre-mRNA molecules which are uniquely expressed in the specific target cells (Puttaraju, DiPasquale et al. 2001). The heterologous gene can either be of therapeutic value to the cell or a toxin which kills the specific cells.

Anti-Sense Compounds

Methods of treating a tumor in a subject include administering a therapeutically effective amount of an anti-sense nucleic acid molecule or ribozymes that may be used to modulate, particularly inhibit, the expression of nucleolin.

Anti-sense nucleic acid molecules are sequence-specific tools capable of selectively modifying or silencing gene expression. Anti-sense oligos function by binding complementary sequences of a specific gene's cognate RNA by Watson-Crick base pairing to form RNA-oligo hybrid molecules (Knorre and Vlassov 1990). Formation of RNA-oligo hybrids interferes with RNA function, stability and consequently protein expression. Various mechanisms have been attributed to the inhibition of protein translation by anti-sense nucleic acid molecules including: interference by physical steric effects and initiation of RNase H-mediated degradation of the double stranded anti-sense-oligo-probe:mRNA hybrid (Dagle and Weeks 2000). Anti-sense oligonucleotide molecules thus are useful therapeutically and as a tool to validate drug targets.

A preferred embodiment of a nucleolin anti-sense DNA has at least 10 nucleotides, preferably between 15 to 25 nucleotides, or a length that binds complementary strands and are most easily formulated and delivered to target organs and cells. Synthetic anti-sense nucleotides preferably contain phosphoester analogs, such as phosphorothioate or thioesters rather than entirely natural phosphodiester bonds as these naturally occurring bonds are labile to nucleases (Shaw, Kent et al. 1991). The phosphorothioate class of oligonucleotides have the additional advantages of high solubility, ease of synthesis, maintenance of Watson-Crick nucleotide hydrogen bonding patterns and the ability to activate RNase H-mediated degradation of cellular mRNA (Stein, Tonkinson et al. 1991; Crooke 1993; Srinivasan and Iversen 1995; Bock, Griffin et al. 1992).

Ribozymes are enzymatic "catalytic" RNA molecules that are self-cleaving and self-splicing (Cech 1986; Altman 1990; Symons 1992). By combining catalytic domains of naturally occurring ribozymes with oligonucleotides specific for a target RNA molecule, artificial catalytic RNA molecules that cleave specific RNA targets can be made. A ribozyme contains at least two functional domains: (1) a specialized sequence for RNA specific binding; and, (2) a catalytic sequence responsible for RNA cleavage (Cech et al., 1992).

Interfering RNA

Tumors and cancers may also be treated by interfering with expression of key regulatory genes by administering interfering RNA compositions. Several embodiments of this technology have now been described, such as synthetic interfering RNA duplexes, synthetic short hairpin RNA duplexes, and gene expression systems enabling the in vivo production and delivery of the interfering RNA molecule (Sharp and Zamore 2000; Bernstein, Caudy et al. 2001; Ketting, Fischer et al. 2001; Sharp 2001; McManus, Petersen et al. 2002; McManus and Sharp 2002; Paddison, Caudy et al. 2002; Paddison, Caudy et al. 2002) (Beach et al., 2001; Fire et al., 2003; Tuschl et al., 2002; Tuschl et al., 2001).

Combination Therapies

In practicing the above-described methods of the present invention, the specific inhibitors (e.g., antibodies, anti-sense, ribozymes, PMTs or interfering RNAs, directed against nucleolin) can be used alone or, preferably, in combination with one another, or with other anti-tumor agents such as radiation, chemotherapeutics, and cytotoxic drugs. Such combination therapy achieves superior and synergistic therapeutic results.

Administration

Pharmaceutical Compositions

A "pharmaceutically acceptable carrier" includes any and all solvents, dispersion media, coatings, antibacterial and antifungal agents, isotonic and absorption delaying agents, and the like, compatible with pharmaceutical administration (Remington 2000). Preferred examples of such carriers or diluents include water, saline, Ringer's solutions and dextrose solution. Supplementary active compounds can also be incorporated into the compositions.

General Considerations

A pharmaceutical composition is formulated to be compatible with its intended route of administration, including intravenous, intradermal, subcutaneous, oral, inhalation, transdermal, transmucosal, and rectal administration. Solutions and suspensions used for parenteral, intradermal or subcutaneous application can include a sterile diluent, such as water for injection, saline solution, polyethylene glycols, glycerine, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Injectable Formulations

Pharmaceutical compositions suitable for injection include sterile aqueous solutions or dispersions for the extemporaneous preparation of sterile injectable solutions or dispersion. For intravenous administration, suitable carriers include physiological saline, bacteriostatic water, CREMOPHOR EL® (BASF; Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a dispersion medium containing, for example, water, polyol (such as glycerol, propylene glycol, and liquid polyethylene glycol), and other compatible, suitable mixtures. Various antibacterial and anti-fungal agents, for example, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin.

Sterile injectable solutions can be prepared by incorporating the anti-nucleolin agents, and other therapeutic components, in the required amount in an appropriate solvent with one or a combination of ingredients as required, followed by sterilization. Methods of preparation of sterile solids for the preparation of sterile injectable solutions include vacuum drying and freeze-drying to yield a solid.

Oral Compositions

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL®, or corn starch; a lubricant such as magnesium stearate or STEROTES®; a glidant such as colloidal silicon dioxide; a sweetening agent such as sucrose or saccharin; or a flavoring agent such as peppermint, methyl salicylate, or orange flavoring.

Compositions for Inhalation

For administration by inhalation, the compounds are delivered as an aerosol spray from a nebulizer or a pressurized container that contains a suitable propellant, e.g., a gas such as carbon dioxide.

Carriers

In one embodiment, the active compounds are prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art.

Transmucosal or Transdermal Formulations

Administration can be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams. Suppositories (e.g., with bases such as cocoa butter and other glycerides) or retention enemas for rectal delivery may also be prepared.

Unit Dosage

Oral formulations or parenteral compositions in unit dosage form can be created to facilitate administration and dosage uniformity. Unit dosage form refers to physically discrete units suited as single dosages for the subject to be treated, containing a therapeutically effective quantity of active compound in association with the required pharmaceutical carrier. The specification for the unit dosage forms of the invention are dictated by, and directly dependent on, the unique characteristics of the active compound and the particular desired therapeutic effect, and the inherent limitations of compounding the active compound.

Dosage

The pharmaceutical composition may further comprise other therapeutically active compounds as noted herein which are usually applied in the treatment of cancers and tumors.

In the treatment or prevention of conditions which require nucleolin modulation, an appropriate dosage level of the therapeutic agent will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

However, the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Determination of the Biological Effect of the Therapeutic

Suitable in vitro or in vivo assays can be performed to determine the effect of a specific therapeutic and whether its administration is indicated for treatment of the affected tissue.

In various specific embodiments, in vitro assays may be performed with representative cells of the type(s) involved in the patient's disorder, to determine if a given therapeutic exerts the desired effect upon the cell type(s). Modalities for use in therapy may be tested in suitable animal model systems including, but not limited to rats, mice, chicken, cows, monkeys, rabbits, dogs and the like, prior to testing in human subjects. Similarly, for in vivo testing, any of the animal model system known in the art may be used prior to administration to human subjects.

The following examples are intended to illustrate the present invention without limitation.

EXAMPLES

Example 1

Immunofluorescent Labeling of Plasma Membrane Nucleolin in Cells

This example illustrates a procedure that stains nuclear nucleolin, or only plasma membrane nucleolin.

Cells from the cell lines DU145 (human prostrate cancer), MDA-MB-231 (human breast cancer) HeLa (human cervical cancer) and HS27 (normal skin fibroblasts) (all available from ATCC; Manassas, Va.) were released from culture substrates with trypsin, resuspended into single cells and plated onto microscope slides. The slides seeded with cells were incubated at 37° C. until they were well attached, as assayed by visual inspection using a microscope. After rinsing the attached cells once with PBS for two minutes, they were fixed in 4% formaldehyde/PBS for at least 15 minutes at 22° C. For nuclear nucleolin staining, cells are permeabilized with 1% Triton X-100 prior to contacting with antibody. After washing twice with PBS, 5 minutes/wash, non-specific binding sites were blocked for 15-60 minutes with 1% NGS/PBS at 22° C., and then incubated with mouse anti-nucleolin antibodies diluted in 1% NGS/PBS or PBS/Tween (0.05%-0.1%) for 1 hour to overnight at 4° C. The samples were washed four times, 5 minutes each with PBS, and then incubated with goat anti-mouse pAb labeled with FITC-labeled secondary antibodies diluted in PBS for 1 hour at 22° C. After again washing four times with PBS for 5 minutes each, the samples were mounted in Mowiol mounting media (prepared as follows: 9 ml/glycerol and 3.36 g Mowiol 40-88 were agitated for 1 h at 22° C. Then, 9 ml of water was then added, and agitation continued for 2 h at 22° C. Tris (0.2 M, pH 8.5; 18 ml) was then added, and the solution incubated for 6 h at 50° C. until the solids were almost completely dissolved. After centrifugation at 5,000×g, the liquid phase was used for mounting), observed under a microscope, and photographed.

Figure 2:
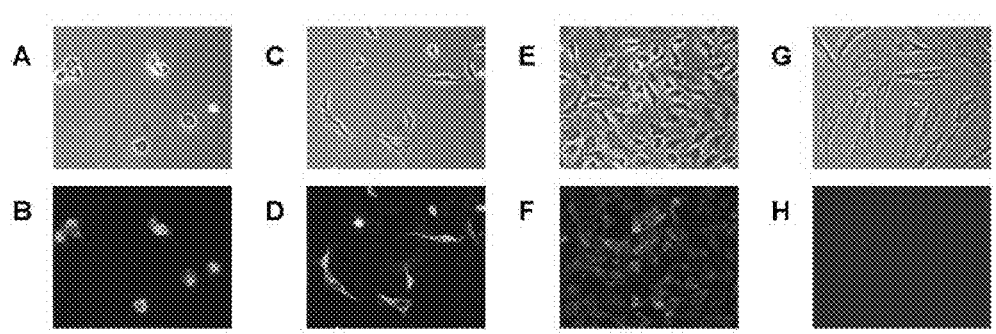
FIG. 2 shows plasma membrane nucleolin staining in the cell lines shown in FIG. 1. Shown are immunofluorescent (B, D, F, H) and parallel phase contrast micrographs (A, C, E, G). Cell lines that were analyzed were: DU145 prostate cancer cells (A, B), MDA-MB-231 breast cancer cells (C, D), HeLa cervical cancer cells (E, F) and HS27 normal skin cells (G, H). An anti-nucleolin antibody was used; the cells were not permeabilized before staining, allowing the antibody access to only the plasma membrane.

FIGS. 1 and 2 show nuclear (FIG. 1) and plasma membrane (FIG. 2) nucleolin staining in the various cell lines. Shown are immunofluorescent (FIGS. 1 and 2; panels B, D, F, H) and parallel phase contrast micrographs (FIGS. 1 and 2; panels A, C, E, G); DU145 cells are shown in A and B; MDA-MB-231 cells are shown in C and D; HeLa cells are shown in E and F; and HS27 cells are shown in G and H. All cell lines show clear nuclear nucleolin staining (FIGS. 1A, 1C, 1E and 1G). Note that when the cells are not permeabilized, thus restricting antibody access to the surface plasma membrane, the normal skin cell line, HS27, is completely negative for plasma membrane staining (FIG. 2H) while cancer cells show strong staining (FIGS. 2B, 2D, 2F and 2H). Staining plasma membrane nucleolin is thus a superior method for diagnosis and prognosis compared to nuclear nucleolin or silver-staining NORs.

Example 2

Correlation of the Degree of Plasma Membrane Nucleolin Expression and Cancer Aggressiveness This experiment demonstrates that cell lines with high levels of plasma membrane nucleolin correspond to those with the most rapid proliferation.

Two cancer cell lines, DU145 and HeLa, and one normal cell line, HS27, were assayed for proliferation rate and compared. Cell doubling time is calculated by determining cell density at regular intervals using the MTT assay (based upon the ability of living cells to reduce 3-(van de Loosdrecht et al., 1994)-2,5 diphenyltetrazolium bromide (MTT) into formazan; (van de Loosdrecht et al., 1994)), and confirmed by counting the cells using trypan blue exclusion.

Figure 3:
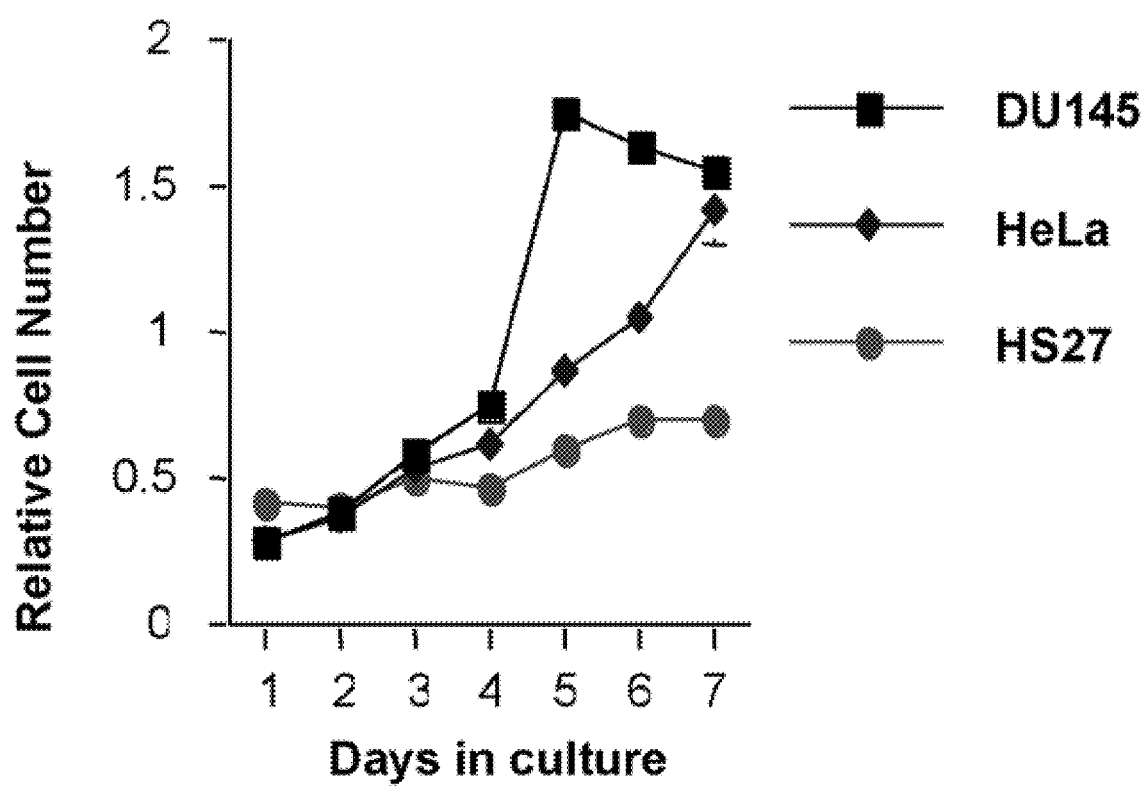
FIG. 3 shows the comparative proliferation rates of cell lines as measured by MTT assay. Square, DU145; diamonds, HeLa; circles, HS27. Although MDA-MB-231 was not included in this experiment, proliferation rates for these four cell lines have been determined to be DU145>MDA-MB-231>HeLa>HS27. Note that the cell lines with high levels of plasma membrane nucleolin correspond to those with the most rapid proliferation (DU145 and HeLa; see FIG. 2).

FIG. 3 shows the comparative proliferation rates of DU145 (squares), HeLa (diamonds) and HS27 (circles) as measured by MTT assay. Until 3 days of culture, growth rates are similar, but after 3 days, HeLa and DU145 increase at a faster rate than the normal HS27 cells. Although MDA-MB-231 was not included in this experiment, proliferation rate has been determined to be DU145>MDA-MB-231>HeLa>HS27. Note that the cell lines with high levels of plasma membrane nucleolin (see FIG. 2) correspond to those with the most rapid proliferation (DU145 and HeLa).

Example 3

Immunofluorescent Labeling of Nucleolin in Paraffin-Embedded Tissue Sections

This example provides a suitable technique to detect and localize nucleolin in a fixed sample that has been embedded.

Sections of cells fixed and embedded in paraffin wax and anchored on microscope slides were washed in three changes of xylene (2 minutes each) to remove the paraffin, hydrated in graded alcohols (series 100%, 95% and 70%; 2 minutes each), and placed in PBS for 5 minutes. Antigen recovery used the approach of low temperature antigen retrieval (LTAR; (Shi et al., 1997; Shi et al., 2001)): After digestion with 0.1% trypsin-EDTA (v/v) (Invitrogen Corp.; Carlsbad, Calif.) diluted in PBS for 15 minutes at 37° C./5% $CO_2$, the samples were washed with deionized water and incubated in 10 mM citrate buffer (pH 6) for 2 hours at 80° C. After cooling, the slides were rinsed with deionized water and then PBS.

Non-specific binding sites were blocked by incubation in 3% BSA in PBS for 30 minutes at 22° C. The samples were then incubated with 4 μg/ml mouse anti-nucleolin mAb (Santa Cruz) diluted in PBS/1% NGS at 4° C. overnight. The samples were then brought to 22° C., washed four times with PBS for 5 minutes, and then reacted with 50 μg/ml Alexa488-conjugated goat anti-mouse IgG (Molecular Probes; Eugene, Oreg.) and 2 μg/ml propidium iodide diluted in PBS/1% NGS for 1 hour at 22° C. After washing four times with PBS for 5 minutes, the samples were mounted in Mowiol mounting medium and observed under a fluorescent microscope.

Figure 4:
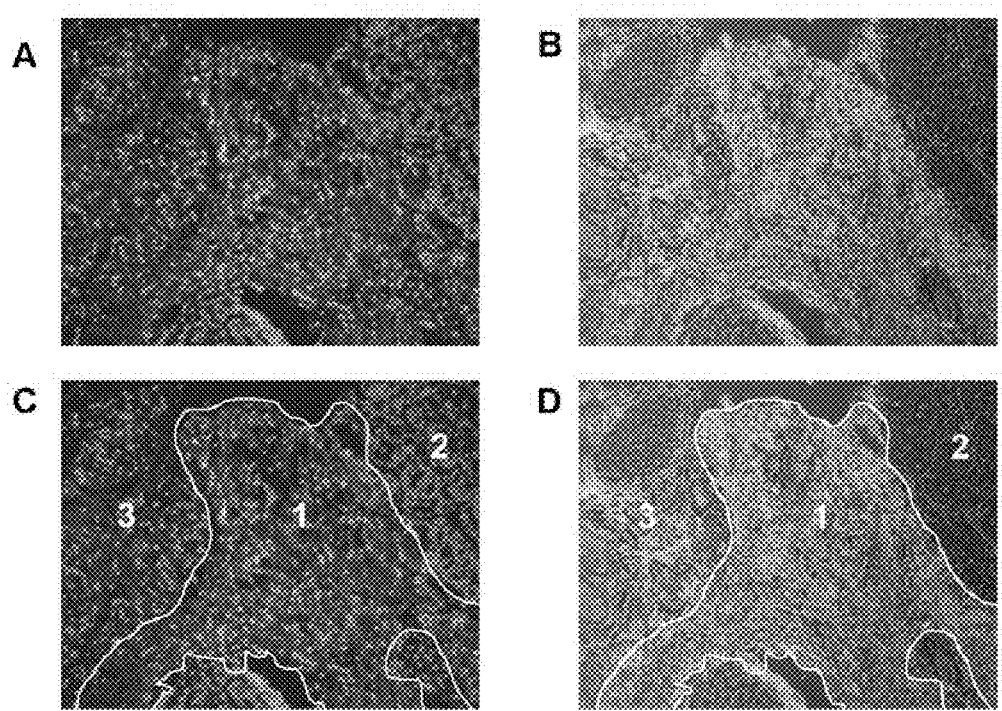
FIG. 4 shows phase contrast (B,D) and immunofluorescent image (A,C) of a paraffin-embedded specimen resected from a patient with squamous cell carcinoma of the head and neck. The specimen was stained for plasma membrane nucleolin and counter-stained with propidium iodide to show cell nuclei. Images (C) and (D) show images (A) and (B) overlaid with markings to better show nucleolin staining. The area 1 encompassed by the white line includes intense nucleolin staining, while the areas outside of 1 show little 3 or no 2 signal.

FIG. 4 shows the results of such an experiment. A clinical sample of a squamous cell carcinoma of the head and neck was prepared and probed for plasma membrane nucleolin. Plasma membrane nucleolin signal was relegated to malignant, neoplastic cells. FIG. 4A shows the immunofluorescent signal obtained from probing for nucleolin; the nuclei are counterstained with a DNA-intercalating dye. FIG. 4B shows a parallel phase contrast micrograph. FIGS. 4C and 4D are duplicates of FIGS. 4A and 4B, except markings have been added to better indicate areas of staining. In region 1, the signal is strong on the cells (faint signal in relation to the nuclear staining in FIG. 4A); these cells are in loosely-organized tissue and are less densely-packed, suggesting that they are malignant. In region 2, normal cells (as delineated by well-packed cells and organized tissue), cells display no plasma membrane nucleolin signal.

Example 4

Plasma Membrane Nucleolin Expression in Lung Carcinoma Cells

This example demonstrates that lung carcinoma cells can be easily identified by staining for plasma membrane nucleolin.

NCI-H1299 (non-small cell lung carcinoma isolated from H. sapiens lymph node; (Giaccone et al., 1992; Lin and Chang, 1996)) and NCI-H82 (small cell lung carcinoma cells, H. sapiens, (Carney et al., 1985; Little et al., 1983; Takahashi et al., 1989)) cells were released from culture substrates with trypsin, resuspended into single cells and plated onto microscope slides. The cells were incubated at 37° C. until they were well-attached as assayed by visual inspection using a microscope. After rinsing the cells once with PBS for 2 minutes, they were fixed in 4% formaldehyde/PBS for at least 15 minutes at 22° C. After washing twice with PBS, 5 minutes/wash, non-specific binding sites were blocked for 15-60 minutes with 1% NGS/PBS at 22° C., and then incubated with mouse anti-nucleolin antibodies for 1 hour to overnight at 4° C. The samples were washed four times, 5 minutes each with PBS and then incubated with goat anti-mouse pAb labeled with FITC-labeled secondary antibodies diluted in PBS with propidium iodide (to stain nuclei) for 1 hour at 22° C. After again washing four times with PBS for 5 minutes each, the samples were mounted in Mowiol mounting media, observed under a microscope and photographed.

Figure 5:
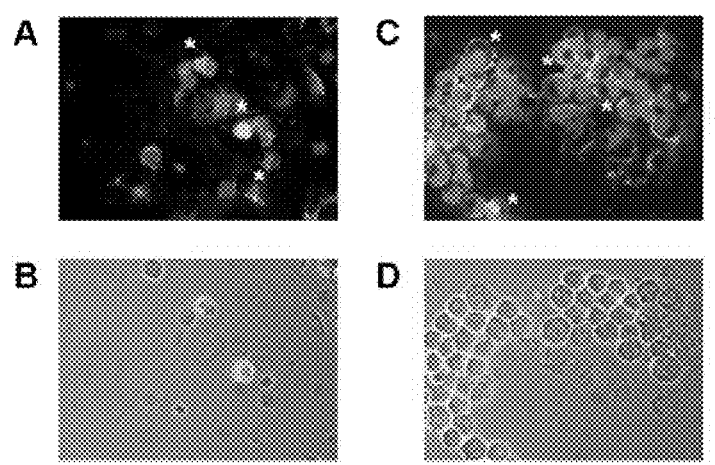
FIG. 5 shows phase contrast (B, D) and immunofluorescent images (A, C) of small cell (NCI-H82) and non-small cell lung (NCI-H1299) cancer cell lines placed onto a microscope slide using a cytospinner. Samples were stained for plasma membrane nucleolin and counter-stained with propidium iodide to show cell nuclei. Cells with exceptionally well-stained plasma membranes are denoted by asterisks (*).

FIG. 5 shows whole cells probed for plasma membrane nucleolin of the two lung cancer cell lines, NCI-H82 (FIG. 5A; a parallel phase contrast image is shown in 5B) and NCI-H1299 (FIG. 5C; a parallel phase contrast image is shown in 5D). In both cell lines, plasma membrane nucleolin staining is strong; examples of well-stained cells are denoted by asterisk (*) in FIGS. 5A and 5C.

Example 5

Plasma Membrane Nucleolin Staining of Clinical Specimens

Figure 6:
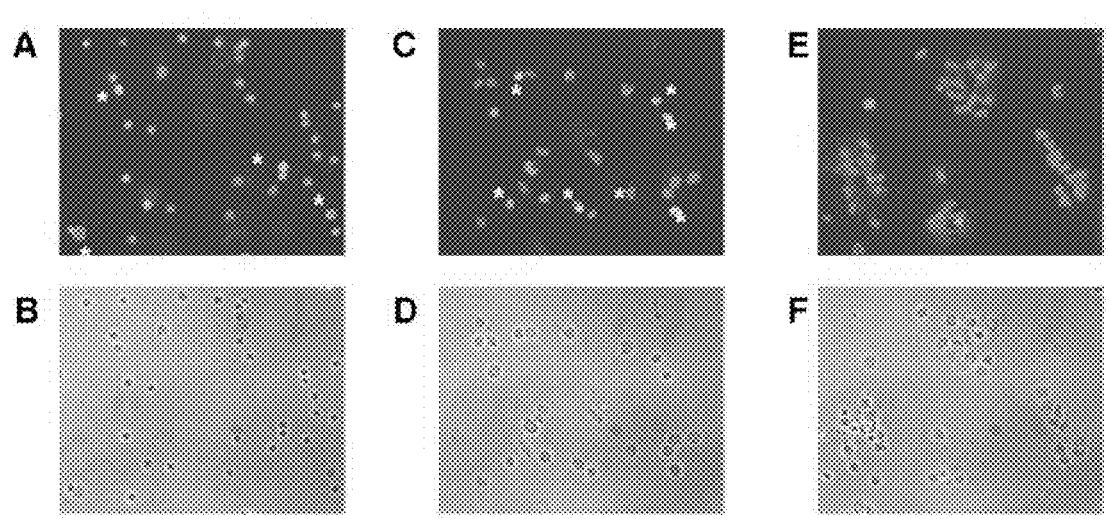
FIG. 6 shows phase contrast (B, D, F) and immunofluorescent images (A, C, E) of peripheral blood (A, B) or bone marrow (C, D and E, F) from human subjects. Samples were stained for plasma membrane nucleolin and counter-stained with propidium iodide to show cell nuclei. Highly stained cells for nucleolin are marked with an asterisk (*); these were only seen in those patients suffering from carcinomas (A,B and C,D), while cells from a healthy patient did not display any plasma membrane nucleolin staining (E, F).

To test the feasibility of using this novel method of assaying plasma membrane nucleolin to diagnose tumor, pre-malignant and malignant cells, clinical specimens from healthy subjects and those suffering from a cancer were collected. Samples from peripheral blood, bone marrow and tumor biopsy samples were obtained and stained for plasma membrane nucleolin as described in Example 4. FIG. 6 shows phase contrast (B, D, F) and immunofluorescent images (A, C, E) of peripheral blood (A, B) or bone marrow (C, D and E, F). Highly stained cells for plasma membrane nucleolin are marked with an asterisk (*); these were only seen in those patients suffering from carcinomas (A,B and C,D), while cells from a healthy patient did not display any plasma membrane staining (E, F).

Example 6

Inhibition of Tumor Growth

A SCID mouse colony was developed using original SCID mice (C.B-17/IcrACSCID) obtained from Taconic (Germantown, N.Y.). The mice were housed in microisolator cages (Allentown Caging Equipment Company, Allentown, N.J.) and maintained under specific pathogen-free conditions. The mice ate NIH31 irradiated pellets (Tekland Premier; Madison, Wis.) and drank autoclaved water. Mice were screened monthly by ELISA serology for mycoplasma, mouse hepatitis virus, pinworms, and Sendai virus. They tested negative.

Female mice 6-8 weeks of age were bled (200 μl) by retro-orbital puncture in order to screen for the presence of mouse immunoglobulin (Ig) using ELISA. Only mice with IgG levels <20 μg/ml were used for the experiments. Mice were weighed once weekly. Tumor cell injections were given SC on the mouse's lower right flank in a total volume of 200 μl. Drug injections were administered by intraperitoneal (IP) injection (200 μl) when tumors were established (Day 6). As tumors developed, SC tumors were measured for tumor volume estimation ($mm^3$) in accordance with the formula (a2× b/2) where a is the smallest diameter and b is the largest diameter. The mice were sacrificed by $CO_2$ and tumors were harvested. Harvested tumors were sliced into 3 mm sections, set in 10% neutral buffered formalin for 24 hours, then placed in 70% ethanol, and embedded in paraffin blocks.

The MDA-MB-231 breast cell line was grown in HyQ RPMI-1640 (1×) media (HyClone, Logan, Utah) with 2.05 mM L-glutamine supplemented with 10% fetal bovine serum (Sigma; St. Louis, Mo.), and maintained in 5% CO2-95% air humidified atmosphere at 37° C. One flask of sub-confluent cells was harvested using 0.25% trypsin-EDTA (HyClone; Logan, Utah) and were counted using the trypan blue assay technique. The other flasks of sub-confluent cells were scraped. Cells (95-100% viability) were re-suspended respectively at a concentration of $8\times10^6$ cells/200 µl of sterile saline.

Taxol 10 mg/kg was prepared and administered IP in the volume of 200 µl every other day for a total of 5 injections in less than an hour from the preparation time. The monoclonal and polyclonal antibodies, mouse IgG, and poly rabbit IgG were prepared and injected within an hour IP in the volume of 200 µl for the initial loading dose of 10 mg/kg. The remaining amount of antibodies were prepared at a maintenance dose of 3 mg/kg in 200 µl, which was aliquoted and frozen into 6 separate tubes per antibody for weekly injections for a total of 6 weeks. Each weekly maintenance dose was thawed and injected within an hour. The PBS 1× control was administered IP in 200 µl weekly for a total of 7 injections. Results of the experiment demonstrate significantly greater tumor regression with the combination of any antibody composition and Taxol.

Example 7 (Prophetic)

Correlation of the Degree of Plasma Membrane Nucleolin Expression and Cancer Aggressiveness Thirty-three lung carcinoma cell lines are analyzed, mostly available from the American Type Culture Collection (Manassas, Va.). Cell doubling time is calculated by determining cell density at regular intervals using the MTT assay and confirmed by counting the cells using trypan blue exclusion. In each experiment HeLa cells (Gey et al., 1952) are included as an internal control. Each value is determined from at least two independent experiments with triplicate samples. To determine levels of nuclear and plasma membrane nucleolin, two methods are implemented. First, nuclear and plasma membrane extracts are prepared from each cell line using methods that have as described (Ausubel et al., 1987; Bates et al., 1999; Yao et al., 1996a). Briefly, cells are harvested and resuspended in a hypotonic buffer, then allowed to swell on ice for several minutes. Cells are lysed using a Dounce homogenizer, and nuclei are collected by centrifugation. Nuclei are resuspended in a high salt buffer to extract nuclear proteins; salt is then removed by dialysis. Plasma membrane proteins can be isolated from the S-100 fraction and are separated from cytosolic proteins and other organelles by centrifugation through a sucrose gradient. Nuclear and PM extracts from different cell are analyzed by Western blot analysis (Ausubel et al., 1987) using an anti-nucleolin antidody (Santa Cruz) followed by chemiluminescent visualization. Nucleolin levels are then quantified by densitometry of the resulting signal recorded on X-ray film and normalized to the intensity of HeLa extract controls. The second approach to determine nucleolin levels involves immunofluorescent probing of the cell lines for nucleolin. Cells are probed for nucleolin surface expression in parallel with DU145 cells (Mickey et al., 1977; Stone et al., 1978) as a positive control, HS27 cells as a negative control and HeLa cells as a reference (see FIG. 2). Cells are photographed and ranked in order of degree of signal, which may also be quantified (using systems that use software and images to quantitate pixels; in this instance, video images are used) or qualitatively evaluated. The data are then subjected to statistical analysis to demonstrate correlations with the degree of cell proliferation (higher rates of cell proliferation indicate more aggressive cancer cells) with the intensity of nucleolin signal across the entire sample and within subsets.

Example 8 (Prophetic)

Lung Cancer Detection

In this example, patient biopsies, sputum samples and resected lung tissue are probed for plasma membrane nucleolin, and these results are compared to other diagnostic and prognostic markers for lung cancer, utilizing archival and routine clinical specimens for this study.

Methods

Specimens including bronchial biopsies, sputum samples, and resected lung tissue are obtained from human subjects, both healthy and those suffering from lung cancer, and each sample encoded such that at the time of nucleolin probing and observation, the sample origin is unknown.

Probing these samples using immunohistochemical techniques are then implemented. For example, plasma membrane nucleolin is probed with one or more anti-nucleolin Abs selected from Table 1, a signal generated from a fluorophore-tagged secondary Ab, and the samples observed and photographed. Appropriate controls include probing with the secondary antibody only, probing with no antibodies, probing with pre-immune serum only, and probing with an antibody known not to react with the cell types being analyzed. To facilitate visualization and localization determination, the cells can be counterstained with Hoechst 33258 or propidium iodide (to visualize nuclei) and/or with fluorescent-tagged phalloidin or phallicidin (to visualize the actin cytoskeleton). The samples are observed, scored (surface signal indicating plasma membrane nucleolin expression) and documented.

All cited publications are incorporated herein by reference. The terms and expressions which have been employed in the present disclosure are used as terms of description and not of limitation, and there is no intention in the use of such terms and expressions of excluding any equivalents of the features shown and described or portions thereof; various modifications are possible and are within the scope of the invention.

REFERENCES

Ausubel, F. M., R. Brent, R. E. Kingston, D. D. Moore, J. G. Seidman, J. A. Smith, and K. Struhl. 1987. Current protocols in molecular biology. John Wiley & Sons, New York.

Babkes, M., A. Ranford, and K. Yaeger. 2001. Sputum trap manifold with nested caps/U.S. Pat. No. 6,325,785.

Bandman, O., H. Yue, N. Corley, and P. Shah. 1999. Human nucleolin-like protein/U.S. Pat. No. 5,932,475.

Bates, P. J., J. B. Kahlon, S. D. Thomas, J. O. Trent, and D. M. Miller. 1999. Antiproliferative activity of G-rich oligonucleotides correlates with protein binding. *J Biol Chem.* 274:26369-77.

Beach, D., E. Bernstein, A. Caudy, S. Hammond, and G. Hannon. 2001. Methods and compositions for RNA interference/WO 01/68836.

Byrne, C. J. 1986. Laboratory tests: implications for nursing care. Addison-Wesley Pub. Co. Health Sciences Division, Menlo Park, Calif. xxi, 756 pp.

Callebaut, C., J. Blanco, N. Benkirane, B. Krust, E. Jacotot, G. Guichard, N. Seddiki, J. Svab, E. Dam, S. Muller, J. P. Briand, and A. G. Hovanessian. 1998. Identification of V3 loop-binding proteins as potential receptors implicated in the binding of HIV particles to CD4(+) cells. *J. Biol Chem.* 273:21988-97.

Carney, D. N., A. F. Gazdar, G. Bepler, J. G. Guccion, P. J. Marangos, T. W. Moody, M. H. Zweig, and J. D. Minna. 1985. Establishment and identification of small cell lung cancer cell lines having classic and variant features. *Cancer Res.* 45:2913-23.

Cech, T., A. Zaug, and M. Been. 1992. RNA ribozyme polymerases, dephosphorylases, restriction endoribo-nucleases and methods/U.S. Pat. No. 5,093,246.

Cole, S. P., E. H. Vreeken, and J. C. Roder. 1985. Antibody production by human X human hybridomas in serum-free medium. *J Immunol Methods.* 78:271-8.

Coligan, J. E. 1996. Current protocols in immunology. Wiley, [New York]. 3 v. (loose leaf) pp.

Davis, K. A., Y. Lin, B. Abrams, and S. D. Jayasena. 1998. Staining of cell surface human CD4 with 2'-F-pyrimidine-containing RNA aptamers for flow cytometry. *Nucleic Acids Res.* 26:3915-24.

Derenzini, M. 2000. The AgNORs. *Micron.* 31:117-20.

Fire, A., S. Kostas, M. Montgomery, L. Timmons, S. Xu, H. Tabara, S. Driver, and C. Mello. 2003. Genetic inhibition by double-stranded RNA/U.S. Pat. No. 6,506,559.

Gey, G., W. Coffman, and M. Kubicek. 1952. Tissue culture studies of the proliferative capacity of cervical carcinoma and normal epithelium. *Cancer Res.* 12:264.

Giaccone, G., J. Battey, A. F. Gazdar, H. Oie, M. Draoui, and T. W. Moody. 1992. Neuromedin B is present in lung cancer cell lines. *Cancer Res.* 52:2732s-2736s.

Ginisty, H., H. Sicard, B. Roger, and P. Bouvet. 1999. Structure and functions of nucleolin. *J Cell Sci.* 112:761-72.

Goding, J. W. 1996. Monoclonal antibodies: Principles and Practice. Academic Press, San Diego. 492 pp.

Harlow, E., and D. Lane. 1988. Antibodies: A laboratory manual. Cold Spring Harbor Laboratory Press, Cold Spring Harbor. 726 pp.

Harlow, E., and D. Lane. 1999. Using antibodies: A laboratory manual. Cold Spring Harbor Laboratory PRess, Cold Spring Harbor, N.Y.

Irving, R. A., G. Coia, A. Roberts, S. D. Nuttall, and P. J. Hudson. 2001. Ribosome display and affinity maturation: from antibodies to single V-domains and steps towards cancer therapeutics. *J Immunol Methods.* 248:31-45.

Jakobovits, A., R. Kucherlapati, S. Klapholz, M. Mendez, and L. Green. 1998. Transgenic mammals having human Ig loci including plural V/WO 98/24893.

Kim, C. S., B. B. Berkley, W. M. Abraham, and A. Wanner. 1982. A micro double capillary method for rheologic measurements of lower airway secretions. *Bull Eur Physiopathol Respir.* 18:915-27.

King, M., and D. Speert. 2002. Use of destran and other polysaccharides to improve mucus clearance/U.S. Pat. No. 6,339,075.

Kohler, G., and C. Milstein. 1975. Continuous cultures of fused cells secreting antibody of predefined specificity. *Nature.* 256:495-7.

Koide, S. 2002. Nucleic acids encoding artificial antibody polypeptides/U.S. Pat. No. 6,462,189.

Langer, P. R., A. A. Waldrop, and D. C. Ward. 1981. Enzymatic synthesis of biotin-labeled polynucleotides: novel nucleic acid affinity probes. *Proc Natl Acad Sci USA.* 78:6633-7.

LaPosta, V., and J. Eldrige. 2001. Adjuvant and vaccine compositions containing monophosphoryl lipid A/U.S. Pat. No. 6,306,404.

Lin, D. L., and C. Chang. 1996. p53 is a mediator for radiation-repressed human TR2 orphan receptor expression in MCF-7 cells, a new pathway from tumor suppressor to member of the steroid receptor superfamily. *J Biol Chem.* 271:14649-52.

Little, C. D., M. M. Nau, D. N. Carney, A. F. Gazdar, and J. D. Minna. 1983. Amplification and expression of the c-myc oncogene in human lung cancer cell lines. *Nature.* 306: 194-6.

Lonberg, N., and R. Kay. 1998. Transgenic non-human animals capable of producing heterologous antibodies/U.S. Pat. No. 5,770,429.

McNicol, A. M., and J. A. Richmond. 1998. Optimizing immunohistochemistry: antigen retrieval and signal amplification. *Histopathology.* 32:97-103.

Mickey, D. D., K. R. Stone, H. Wunderli, G. H. Mickey, R. T. Vollmer, and D. F. Paulson. 1977. Heterotransplantation of a human prostatic adenocarcinoma cell line in nude mice. *Cancer Res.* 37:4049-58.

Miller, D., P. Bates, and J. Trent. 2000. Antiproliferative activity of G-rich oligonucleotides and method of using same to bind to nucleolin/WO 00/61597.

Mitchell, L. 1997. Therapeutic molecules generated by trans-splicing/WO 09/722,250.

Naito, M., H. Hamada, and T. Tsuruo. 1988. ATP/Mg2+-dependent binding of vincristine to the plasma membrane of multidrug-resistant K562 cells. *J Biol Chem.* 263:11887-91.

Orfao, A., and A. Ruiz-Arguelles. 1996. General concepts about cell sorting techniques. *Clin Biochem.* 29:5-9.

Robinson, J. M., and D. D. Vandre. 2001. Antigen retrieval in cells and tissues: enhancement with sodium dodecyl sulfate. *Histochem Cell Biol.* 116:119-30.

Rubin, B., and M. Newhouse. 1999. Use of surface active agents to promote mucus clearance/U.S. Pat. No. 5,925, 334.

Sharon, J. 1995. Polyclonal antibody libraries/WO 95/20401.

Shi, S. R., R. J. Cote, and C. R. Taylor. 1997. Antigen retrieval immunohistochemistry: past, present, and future. *J Histochem Cytochem.* 45:327-43.

Shi, S. R., R. J. Cote, and C. R. Taylor. 2001. Antigen retrieval techniques: current perspectives. *J Histochem Cytochem.* 49:931-7.

Singh, S., and P. Dias. 2002. Transgenic avian species for making human and chimeric antibodies/US 2002/ 0028488.

Sorokina, E. A., and J. G. Kleinman. 1999. Cloning and preliminary characterization of a calcium-binding protein closely related to nucleolin on the apical surface of inner medullary collecting duct cells. *J Biol Chem.* 274:27491-6.

Srivastava, M., and H. B. Pollard. 1999. Molecular dissection of nucleolin's role in growth and cell proliferation: new insights. *Faseb J.* 13:1911-22.

Stedman, T. L. 2000. Stedman's medical dictionary. Lippincott Williams & Wilkins, Philadelphia. xxxvi, [127], 2098 p. pp.

Stone, K. R., D. D. Mickey, H. Wunderli, G. H. Mickey, and D. F. Paulson. 1978. Isolation of a human prostate carcinoma cell line (DU 145). *Int J. Cancer.* 21:274-81.

Surani, A., M. Neuberger, and M. Bruggemann. 1996. Production of antibodies from transgenic animals/U.S. Pat. No. 5,545,807.

Takahashi, T., M. M. Nau, I. Chiba, M. J. Birrer, R. K. Rosenberg, M. Vinocour, M. Levitt, H. Pass, A. F. Gazdar, and J.

D. Minna. 1989. p53: a frequent target for genetic abnormalities in lung cancer. *Science.* 246:491-4.

Tuschl, T., S. Elbashir, and W. Lendeckel. 2002. RNA interference mediating small RNA molecules/WO 02/44,321.

Tuschl, T., P. Sharp, P. Zamore, and D. Bartel. 2001. RNA sequence-specific mediators of RNA interference/WO 01/075,164.

Tuteja, R., and N. Tuteja. 1998. Nucleolin: a multifunctional major nucleolar phosphoprotein. *Crit. Rev Biochem Mol Biol.* 33:407-36.

van de Loosdrecht, A. A., R. H. Beelen, G. J. Ossenkoppele, M. G. Broekhoven, and M. M. Langenhuijsen. 1994. A tetrazolium-based colorimetric MTT assay to quantitate human monocyte mediated cytotoxicity against leukemic cells from cell lines and patients with acute myeloid leukemia. *J Immunol Methods.* 174:311-20.

Wysocki, L. J., and V. L. Sato. 1978. "Panning" for lymphocytes: a method for cell selection. *Proc Natl Acad Sci USA.* 75:2844-8.

Xu, X., F. Hamhouyia, S. D. Thomas, T. J. Burke, A. C. Girvan, W. G. McGregor, J. O. Trent, D. M. Miller, and P. J. Bates. 2001. Inhibition of DNA Replication and Induction of S Phase Cell Cycle Arrest by G-rich Oligonucleotides. *J Biol Chem.* 276:43221-30.

Yao, G. Q., S. Corrias, and Y. C. Cheng. 1996a. Identification of two oligodeoxyribonucleotide binding proteins on plasma membranes of human cell lines. *Biochem Pharmacol.* 51:431-6.

Yao, G. Q., S. Corrias, and Y. C. Cheng. 1996b. Identification of two oligodeoxyribonucleotide binding proteins on plasma membranes of human cell lines. *Biochem Pharmacol.* 51:431-6.

The invention claimed is:

1. A method of treating cancer in a subject comprising administering to said subject a therapeutically effective amount of an anti-nucleolin antibody and a pharmaceutically acceptable carrier, wherein said nucleolin antibody is substantially non-immunogenic to human.

2. The method of claim 1, further comprising administering to said subject a chemotoxic or chemotherapeutic agent.

3. The method of claim 1, further comprising treating said subject with radiation therapy.

4. The methods of claim 2 wherein said chemotoxic or chemotherapeutic agent is selected from the group consisting of cyclophosphamide, etoposide, doxorubicin, methotrexate, vincristine, procabazine, prednisone, dexamethasone, tamoxifen citrate, carboplatin, cisplatin, oxaliplatin, 5-fluorouracil, camptothecin, zoledronic acid, Ibandronate and mytomicin.

5. A method of treating cancer in a subject comprising administering to said subject a therapeutically effective amount of an antinucleolin antibody, a chemotoxic or chemotherapeutic agent and a pharmaceutically acceptable carrier.

6. The method of claim 5, wherein said chemotoxic or chemotherapeutic agent is selected from the group consisting of cyclophosphamide, etoposide, doxorubicin, methotrexate, vincristine, procabazine, prednisone, dexamethasone, tamoxifen citrate, carboplatin, cisplatin, oxaliplatin, 5-fluorouracil, camptothecin, zoledronic acid, Ibandronate and mytomicin.

7. A method of treating cancer in a subject comprising administering to said subject a therapeutically effective amount of an antinucleolin antibody and a pharmaceutically acceptable carrier, and further treating said subject with radiation therapy.

* * * * *

UNITED STATES PATENT AND TRADEMARK OFFICE
CERTIFICATE OF CORRECTION

PATENT NO. : 8,029,784 B2
APPLICATION NO. : 12/041969
DATED : October 4, 2011
INVENTOR(S) : Paula J. Bates et al.

It is certified that error appears in the above-identified patent and that said Letters Patent is hereby corrected as shown below:

On the Title Page, Item (56) Other Publications

Col. 2, line 19, please delete "With" and insert --with--

Page 2, Item (56) Other Publications

Col. 1, line 4, please delete "ply(ADP-ribose)" and insert --poly(ADP-ribose)--

Page 3, Item (56) Other Publications

Col. 1, line 38, please delete "Dna" and insert --DNA--
Col. 2, line 26, please delete "d(Cgg)n." and insert --d(Cgg)n--

Page 4, Item (56) Other Publications

Col. 1, line 31, please delete "MRLI/Ipr" and insert --MRL/Ipr--
Col. 1, line 43, please delete "ELISApIus" and insert --ELISAplus--
Col. 1, line 64, please delete "USO4" and insert --US04--
Col. 2, line 18, please delete "Nati" and insert --Natl--
Col. 2, line 58, please delete "and and" and insert --and--

Page 6, Item (56) Other Publications

Col. 1, line 1, please delete "a" and insert --A--
Col. 1, line 2, please delete "a" and insert --A--

Signed and Sealed this
Twenty-seventh Day of May, 2014

Michelle K. Lee
*Deputy Director of the United States Patent and Trademark Office*

CERTIFICATE OF CORRECTION (continued)
U.S. Pat. No. 8,029,784 B2

Page 6, Item (56) Other Publications (cont.)

Col. 2, line 33, please delete "Bioassays" and insert --Bioessays--

Page 7, Item (56) Other Publications

Col. 2, line 39, please delete "injibit" and insert --inhibit--
At the end of Col. 2, please insert the following:

--Gougeon, M-L. et al., "Programmed cell death in peripheral lymphocytes from HIV-infected persons", The Journal of Immunology, vol. 156, pp. 3509-3520, (1996).--

UNITED STATES PATENT AND TRADEMARK OFFICE
CERTIFICATE OF CORRECTION

| | | |
|---|---|---|
| PATENT NO. | : 8,029,784 B2 | Page 1 of 1 |
| APPLICATION NO. | : 12/041969 | |
| DATED | : October 4, 2011 | |
| INVENTOR(S) | : Paula J. Bates et al. | |

It is certified that error appears in the above-identified patent and that said Letters Patent is hereby corrected as shown below:

In the Specification:

Col. 1, Line 12, please insert as follows:

--FEDERALLY SPONSORED RESEARCH OR DEVELOPMENT--

--This invention was made with government support under 1 R21 CA 91115 awarded by the National Institutes of Health, DAMD17-98-1-8583 awarded by the Department of Defense, and DAMD17-01-1-0067 awarded by the Department of Defense. The government has certain rights in the invention.--

Signed and Sealed this
Twenty-ninth Day of September, 2015

Michelle K. Lee
*Director of the United States Patent and Trademark Office*